(12) United States Patent
Soukup et al.

(10) Patent No.: US 8,445,708 B2
(45) Date of Patent: May 21, 2013

(54) PROCESS FOR PREPARING CHIRAL OCTENOIC ACID DERIVATIVES

(75) Inventors: Milan Soukup, Bottmingen (CH); Karl Reuter, Gundelfingen (DE); Florian Stolz, Freiburg (DE); Viktor Meier, Gundelfingen (DE); Jofzsef Balint, Gundelfingen (DE); Mark Kantor, Freiburg (DE)

(73) Assignee: Reuter Chemischer Apparatebau KG, Freiburg (DE)

( * ) Notice: Subject to any disclaimer, the term of this patent is extended or adjusted under 35 U.S.C. 154(b) by 644 days.

(21) Appl. No.: 12/091,795

(22) PCT Filed: Oct. 27, 2006

(86) PCT No.: PCT/EP2006/010361
§ 371 (c)(1),
(2), (4) Date: Oct. 21, 2008

(87) PCT Pub. No.: WO2007/048620
PCT Pub. Date: May 3, 2007

(65) Prior Publication Data
US 2009/0221848 A1     Sep. 3, 2009

(30) Foreign Application Priority Data

Oct. 28, 2005 (DE) .......................... 10 2005 052 195

(51) Int. Cl.
*C07C 59/147* (2006.01)
*C07C 59/00* (2006.01)
*C07C 231/00* (2006.01)

(52) U.S. Cl.
USPC ........... 554/116; 562/465; 562/598; 564/139; 564/161; 514/557

(58) Field of Classification Search
None
See application file for complete search history.

(56) References Cited

U.S. PATENT DOCUMENTS

| | | |
|---|---|---|
| 5,559,111 A | 9/1996 | Göschke et al. |
| 5,606,078 A | 2/1997 | Göschke et al. |
| 6,777,574 B1 | 8/2004 | Herold et al. |
| 7,009,078 B1 | 3/2006 | Herold et al. |
| 7,132,569 B2 | 11/2006 | Herold et al. |
| 7,772,405 B2 | 8/2010 | Sedelmeier et al. |
| 2004/0024151 A1 | 2/2004 | Becker et al. |

FOREIGN PATENT DOCUMENTS

| | | |
|---|---|---|
| EP | 0 678 503 B1 | 10/1995 |
| EP | 0 678 514 A1 | 10/1995 |
| EP | 1 582 523 A1 | 10/2005 |
| JP | 2009-500435 A | 1/2009 |
| JP | 2009-514808 A | 4/2009 |
| WO | WO 01/09079 A1 | 2/2001 |

(Continued)

OTHER PUBLICATIONS

Dorwald, F., Side Reactions in Organic Synthesis, 2005, Wiley-VCH, (20 pages).*

(Continued)

*Primary Examiner* — Yatek K Cutliff
(74) *Attorney, Agent, or Firm* — Paul D. Strain, Esq.; Strain & Strain PLLC

(57) ABSTRACT

The invention relates to a process for preparing chiral octenoic acid derivatives, which constitute important intermediates in the preparation of medicament active ingredients, and also to novel intermediates which are used in the process for preparing the octenoic acid derivatives mentioned.

16 Claims, 5 Drawing Sheets

FOREIGN PATENT DOCUMENTS

| | | |
|---|---|---|
| WO | WO 01/09083 A1 | 2/2001 |
| WO | WO 02/02487 A1 | 1/2002 |
| WO | WO 02/02500 A1 | 1/2002 |
| WO | WO 02/02508 A1 | 1/2002 |
| WO | WO 02/08172 A1 | 1/2002 |
| WO | WO 02/14414 A2 | 2/2002 |
| WO | WO 02/092828 A2 | 11/2002 |
| WO | WO 03/103653 A1 | 12/2003 |
| WO | WO 2004/089915 A1 | 10/2004 |
| WO | WO 2007/006532 A1 | 1/2007 |
| WO | WO 2007/045420 A2 | 4/2007 |

OTHER PUBLICATIONS

Diaz et al., "A Stereoselective Synthesis of (R)-(−)-Rolipram from L-Glutamic Acid", Synthesis, May 1997, pp. 559-562.

Krasovskiy et al., "A LiCl-Mediated Br/Mg Exchange Reaction for the Preparation of Funtionalized Aryl- and Heteroarylmagnesium Compounds from Organic Bromides", Angew. Chem. Int. Ed. vol. 43 (2004), pp. 3333-3336.

Durham et al., "Methyl Hydrogen Hendecandedioate", Organic Syntheses, Coll. vol. 4 (1963); vol. 38 (1958), p. 55.

Nishiguchi et al., "Selective monoesterification of dicarboxylic acids catalysed by ion-exchange resins", J. Chem. Soc., Perkin Trans. 1 (1999), pp. 3023-3027.

Blum et al., "Design, Synthesis, and Biological Evaluation of Substituted 2-Cyclohexyl-4-phenyl-1$H$-imidazoles: Potent and Selective Neuropeptide Y Y5-Receptor Antagonists", J. Med. Chem. vol. 47 (2004), pp. 2318-2325.

Conde et al., "Synthesis of SB 222618. A potential PDE IV inhibitor", Tetrahedron Letters vol. 41 (2000), pp. 811-814.

March et al., "Advanced Organic Chemistry", $4^{th}$ Edition (1992), pp. 1209-1211.

Japanese Office Action dated May 11, 2012, 3 pgs, JP 2009/513591.

Soukup, U.S. PTO Office Action, U.S. Appl. No. 13/422,144, Jul. 9, 2012, 11 pgs.

Soukup, U.S. PTO Notice of Allowance, U.S. Appl. No. 13/422,144, Feb. 4, 2013, 12 pgs.

Japanese Office Action with German translation, Application No. 2008-537007, Dec. 12, 2012 (mail date Dec. 14, 2012), 3 pgs.

* cited by examiner

PROCESS FOR PREPARING CHIRAL OCTENOIC ACID DERIVATIVES

The invention relates to a process for preparing chiral octenoic acid derivatives which constitute important intermediates in the preparation of medicament active ingredients. The invention also relates to novel intermediates which are used in the process for preparing the octenoic acid derivatives mentioned.

BACKGROUND OF THE INVENTION

Documents WO 02/02508, WO 02/08172 and WO 01/09083 describe chiral octenoic acid derivatives of the general formula (I) as important intermediates especially in the multistage preparation of the renin inhibitor known as "aliskiren" (CAN: 173334-57-1) from Novartis. According to these documents, the chiral phenyl-substituted octenoic acid derivatives are formed from two chiral blocks, one unit being a chiral 3-phenyl-2-isopropylpropyl halide (known from WO 02/02487 and WO 02/02500) and the other unit being a chiral 5-halo-2-isopropylpent-4-enoic acid (described in WO 01/09079 and WO 02/092828), which are combined to give the desired product. The two chiral blocks are prepared separately via complex multistage syntheses, as described in the abovementioned documents. The overall preparation process for the chiral phenyl-substituted octenoic acid derivatives of the general formula (I) is thus very complex, and additionally includes an asymmetric hydrogenation step in which a very expensive homogeneous chiral Rh catalyst which is not readily available is needed, which makes the process very costly overall.

BRIEF SUMMARY OF THE INVENTION

It was thus an object of the present invention to provide a simplified preparation process for octenoic acid derivatives of the general formula (I).

The object stated is achieved by a process for preparing compounds of the general formula (I)

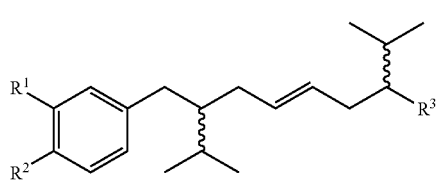

in which
$R^1$ and $R^2$ are each independently hydroxyl, alkoxy, aryloxy, arylalkyloxy or alkoxyalkoxy;
$R^3$ is a heterocarbon group containing at least one heteroatom selected from O and N with at least one carbon-heteroatom multiple bond at the C-1 position, such as $COOR^6$
in which $R^6$ is hydrogen, alkyl, aryl, arylalkyl or trialkylsilyl;
nitrile;
$C(O)R^7$,
in which $R^7$ is hydrogen, halogen, $O^-$, OM,
in which M is an alkali metal or an equivalent of an alkaline earth metal,
$OCOR^{12}$, in which $R^{12}$ is branched lower alkyl having from 1 to 5 carbon atoms, preferably pivaloyl, $OCOCF_3$, $OSO_2CH_3$ or $OSO_2CF_3$
or is a protecting or activating group such as C(O)N-alkyl-O-alkyl or $C(O)NR^4R^5$,
in which $R^4$ and $R^5$ are each independently hydrogen, alkyl, aryl, arylalkyl, trialkylsilyl or the like, or $R^4$ and $R^5$ together with the nitrogen form a five- to six-membered heterocyclic ring system which may optionally have from 1 to 3 additional heteroatoms;
or salts thereof,
wherein a compound of the general formula (II)

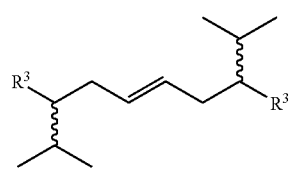

in which
$R^3$ is in each case independently as defined above under the formula (I);
is reacted in an addition reaction with a compound of the formula (III)

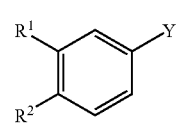

in which
Y is halogen, metal, metal halide, metal alkoxide or metal carboxylate,
$R^1$ and $R^2$ are each as defined above under the formula (I),
or
Y is hydrogen, and
$R^1$ is a protected hydroxyl function, such as a trifluoromethanesulfonate or trifluoroacetate group;
$R^2$ is as defined above under the formula (I),
to obtain a compound of the formula (IV)

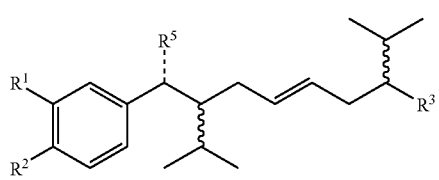

in which
$R^1$, $R^2$ and $R^3$ are each as defined above under the formula (I);
the dotted line represents a single or double bond;
$R^5$ is O or $NR^8$ in which $R^8$ is hydrogen or alkyl if the dotted line represents a double bond, or
$R^5$ is OH or $NR^8R^9$ in which $R^8$ and $R^9$ are each independently hydrogen or alkyl if the dotted line represents a single bond;

and the compound of the formula (IV) is subjected to at least one reduction reaction to obtain the desired product of the formula (I);

or the compound of the general formula (II) is subjected to at least one reduction reaction to obtain the compound of the formula (V)

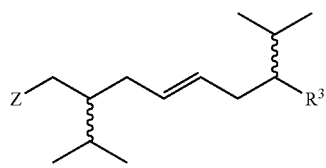

(V)

in which $R^3$ is as defined above under formula (I);

Z is a leaving group, such as halogen, mesyl, tosyl or triflate;

and the compound of the formula (IV) is reacted in an addition reaction with a compound of the formula (III) to obtain the desired product of the formula (I).

In a preferred embodiment of the process according to the invention, the compound of the formula (II) is used as a mixture of the stereoisomers.

The process according to the invention preferably comprises an isomer separation step before or after one of the addition or reduction steps. The isomers can be separated in a manner known per se, for example by various crystallization techniques, chromatography, etc., in one or more steps. In a further preferred embodiment, the process according to the invention comprises, as well as the isomer separation step mentioned, additionally an isomerization or racemization of the undesired isomers.

Advantageously, the radicals in the formula (I) are defined as follows:

$R^1$: hydroxyl or branched or unbranched lower alkoxy having from 1 to 5 carbon atoms, such as methoxy, ethoxy, n- and i-propoxy, n-, i- and t-butoxy or pentoxy, aryloxy such as phenyloxy, naphthyloxy or derivatives thereof, or benzyloxy or branched or unbranched alkoxyalkoxy having in each case from 1 to 5, preferably from 1 to 2 carbon atoms in the alkoxy group, such as 1-methoxymethoxy, 1-methoxy-2-ethoxy, 1-methoxy-3-propoxy, 1-methoxy-4-butoxy, etc., more particularly 1-methoxymethoxy, 1-methoxy-2-ethoxy, 1-methoxy-3-propoxy, 1-methoxy-4-butoxy, especially 1-methoxy-3-propoxy, $R^2$: hydroxyl or branched or unbranched lower alkoxy having from 1 to 5 carbon atoms, such as methoxy, ethoxy, n- and i-propoxy, n-, i- and t-butoxy or pentoxy, aryloxy such as phenyloxy, naphthyloxy or derivatives thereof, or benzyloxy or branched or unbranched alkoxyalkoxy having in each case from 1 to 5, preferably from 1 to 2 carbon atoms in the alkoxy group, such as 1-methoxymethoxy, 1-methoxy-2-ethoxy, 1-methoxy-3-propoxy, 1-methoxy-4-butoxy, etc., more preferably methoxy, and $R^3$: COOR$^6$ in which $R^6$ is hydrogen, branched or unbranched lower alkyl having from 1 to 5 carbon atoms, aryl, benzyl or trialkylsilyl, nitrile, C(O)R$^7$ in which $R^7$ is halogen, OM in which M is an alkali metal or an equivalent of an alkaline earth metal, or C(O)NR$^4$R$^5$ in which $R^4$ and $R^5$ are each independently branched or unbranched lower alkyl having from 1 to 5 carbon atoms, or benzyl.

The process according to the invention more preferably serves to prepare the compound of the formula (VI)

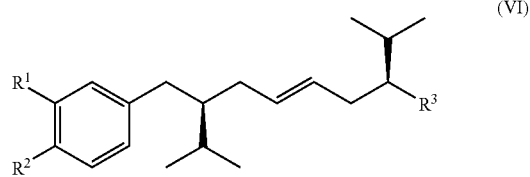

(VI)

in which $R^1$, $R^2$ and $R^3$ are each as defined above under formula (I).

In particular, the process according to the invention serves to prepare the compound of the formula (VII)

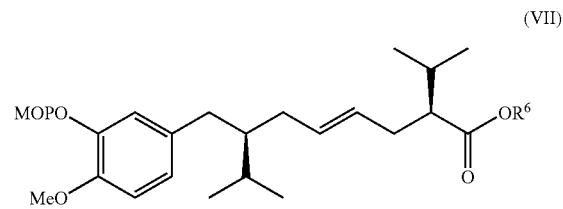

(VII)

in which

MOPO is methoxypropoxy and $R^6$ is as defined above under formula (I).

In a further preferred variant of the process according to the invention, $R^3$ is independently carboxyl or nitrite.

The addition reaction is preferably carried out with a compound of the formula (III) in which Y represents various metals, such as alkali metals, or metal halide or metal alkoxide or metal carboxylate, in which the metal may be Mg, Al, B, Mn, Cu, Cd, Zn and Sn. More preferably, Y is Li, Na, CuCl, CuBr, CuI, MgCl or MgBr.

The reduction is carried out in one or two steps, for example with metal hydrides or trialkylsilane in the presence of acids or with Lewis acids.

In a further preferred embodiment of the process according to the invention, the compound of the formula (VII) is converted in an additional amidation in a known manner to the compound of the formula (VIII)

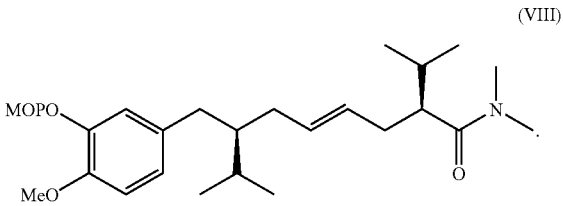

(VIII)

If the addition is carried out with a compound of the formula (III) in which Y is hydrogen and $R^1$ is a protected hydroxyl function and $R^2$ is as defined above under formula (I), the process according to the invention preferably comprises a further alkylation step for converting $R^1$ to alkoxy or alkoxyalkoxy.

The invention further relates to compounds of the formula (IIa)

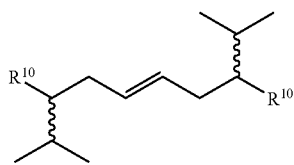

(IIa)

in which
R¹⁰ is a heterocarbon group containing at least one heteroatom selected from O and N with at least one carbon-heteroatom multiple bond at the C-1 position, such as
COOR⁶ in which R⁶ is hydrogen, alkyl, aryl, arylalkyl or trialkylsilyl;
nitrile;
C(O)R⁷,
in which R⁷ is hydrogen, halogen, O⁻, OM,
in which M is an alkali metal or an equivalent of an alkaline earth metal,
OCOR¹²,
in which R¹² is branched lower alkyl having from 1 to 5 carbon atoms, preferably pivaloyl, or
OCOCF₃, OSO₂CH₃ or OSO₂CF₃
or is a protecting or activating group such as C(O)N-alkyl-O-alkyl or C(O)NR⁴R⁵,
in which R⁴ and R⁵ are each independently hydrogen, alkyl, aryl, arylalkyl, trialkylsilyl or the like, or R⁴ and R⁵ together with the nitrogen atom form a five- to six-membered heterocyclic ring system which may optionally have from 1 to 3 additional heteroatoms;
where R⁴ and R⁵ together with the nitrogen cannot be a 4(S)-substituted oxazolidin-2-on-3-yl in each R¹⁰ if both radicals are C(O)NR⁴R⁵,
or salts thereof.

A preferred group of the compounds according to the invention of the formula (IIa) is that of (S,S)-enantiomers of the formula (IIb)

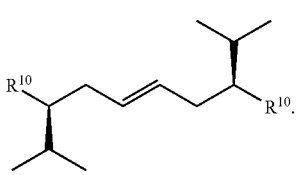

(IIb)

In a further preferred group of compounds according to the invention of the formula (IIa) or (IIb), R¹⁰ is C(O)R⁷ in which R⁷ is hydrogen, halogen, O⁻, OM in which M is an alkali metal, an equivalent of an alkaline earth metal, OCOR¹² in which R¹² is branched lower alkyl having from 1 to 5 carbon atoms, preferably pivaloyl, or OCOCF₃, OSO₂CH₃ or OSO₂CF₃, nitrile or COOR⁶ in which R⁶ is as defined above under formula (I), and is preferably hydrogen.

More preferably, R¹⁰ is in each case independently nitrile or COCl or COBr or COOR⁶ in which R⁶ is as defined above under formula (I), and is preferably hydrogen.

The invention further relates to compounds of the formula (IV)

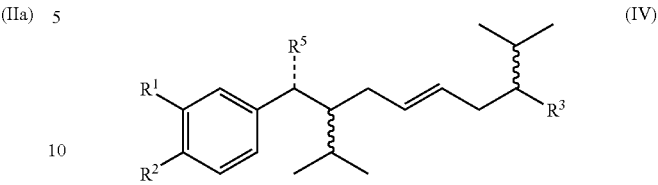

(IV)

in which
R¹, R² and R³ are each as defined above under the formula (I);
the dotted line represents a single or double bond;
R⁵ is O or NR⁸ in which R⁸ is hydrogen or alkyl if the dotted line represents a double bond, or
R⁵ is OH or NH₂ if the dotted line represents a single bond, or salts thereof, preferably the (S,S)-enantiomers. In the context of the present invention, the preferred (S,S)-enantiomers are understood to mean compounds in which the isopropyl groups of the octane side chains have the following configuration:

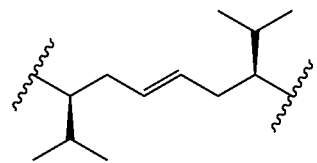 [SMILES: *[C@@H](C/C=C/C[C@H](*)C(C)C)C(C)C]

The (S,S)-enantiomers mentioned can advantageously be converted to compounds of the formula (I) with retention of the two chiral centers.

In the context of the present invention, the expression "halogen" relates to chlorine, bromine, iodine.

"Alkyl" relates, unless stated otherwise, to straight-chain or branched or cyclic saturated hydrocarbons or combinations thereof with preferably from 1 to 20 carbon atoms, especially from 1 to 10 carbon atoms, more preferably from 1 to 5 carbon atoms. Examples of such alkyl groups (provided that the designated length includes the specific example) are methyl, ethyl, propyl, isopropyl, butyl, sec-butyl, tert-butyl, pentyl, isopentyl, neopentyl, tert-pentyl, 1-methylbutyl, 2-methylbutyl, 3-methylbutyl, hexyl, isohexyl, heptyl and octyl.

"Alkoxy" relates to straight-chain or branched saturated alkyl which is bonded via oxygen and has preferably from 1 to 20 carbon atoms, especially from 1 to 10 carbon atoms, more preferably from 1 to 5 carbon atoms, most preferably from 1 to 2 carbon atoms. Examples of such alkoxy groups (provided that the designated length includes the specific example) are methoxy, ethoxy, propoxy, isopropoxy, butoxy, isobutoxy and tert-butoxy.

The alkyl and alkoxy groups may be substituted by one or more of the following groups selected from halogen, hydroxyl, cyano, C₁-C₆-alkoxy, nitro, amino, C₁-C₆-alkylamino, di-C₁-C₆-alkylamino, carboxyl, C₁-C₆-alkoxycarbonyl, aminocarbonyl, halomethyl, dihalomethyl, trihalomethyl, haloethyl, dihaloethyl, trihaloethyl, tetrahaloethyl, pentahaloethyl.

The term "cycloalkyl" represents, unless stated otherwise, an organic radical which is derived from a monocyclic (C₃-C₇)-cycloalkyl compound by removal of one hydrogen radical from one ring carbon atom of the cycloalkyl compound. Examples of cycloalkyl groups are cyclopropyl, cyclobutyl, cyclopentyl, cyclohexyl, cycloheptyl, cyclopropenyl, cyclobutenyl, cyclopentenyl, cyclohexenyl, cycloheptenyl, 1,3-cyclobutadienyl, 1,3-cyclopentadienyl, 1,3-cyclohexadienyl, 1,4-cyclohexadienyl, 1,3-cycloheptadienyl, 1,4-cycloheptadienyl, bicyclo[3.2.1]octane and bicyclo[2.2.1]heptane. The term "cycloalkyl" also encompasses cycloalkenyl groups having one or two double bonds.

The expression "heterocyclic" denotes a monocyclic, heterocyclic ring system. Monocyclic heterocyclic rings consist of from about 3 to 7 ring atoms with from 1 to 5 heteroatoms selected from N, O and S, and preferably from 3 to 7 atoms in the ring. Bicyclic heterocycles consist of from about 5 to 17 ring atoms, preferably from 5 to 12 ring atoms.

The expression "aryl" denotes a cyclic or polycyclic ring consisting of from 6 to 12 carbon atoms, which may be unsubstituted or is substituted by one or more substituent groups which are specified above for the alkyl and alkoxy groups. Examples of aryl groups are phenyl, 2,6-dichlorophenyl, 3-methoxyphenyl, naphthyl, 4-thionaphthyl, tetralinyl, anthracenyl, phenanthrenyl, benzonaphthenyl, fluorenyl, 2-acetamidofluoren-9-yl and 4'-bromobiphenyl.

The expression "heteroaryl" denotes an aromatic cyclic or polycyclic ring system having from 1 to 9 carbon atoms and from 1 to 4 heteroatoms selected from N, O and S. Typical heteroaryl groups are 2- or 3-thienyl, 2- or 3-furanyl, 2- or 3-pyrrolyl, 2-, 4-, or 5-imidazolyl, 3-, 4- or 5-pyrazolyl, 2-, 4- or 5-thiazolyl, 3-, 4-, or 5-isothiazolyl, 2-, 4- or 5-oxazolyl, 3-, 4- or 5-isoxazolyl, 3- or 5-1,2,4-triazolyl, tetrazolyl, 2-, 3- or 4-pyridinyl, 3-, 4- or 5-pyridazinyl, 2-pyrazinyl, 2-, 4- or 5-pyrimidinyl. The heteroaryl groups may be unsubstituted or substituted by from 1 of 3 of the substituents as specified above for the alkyl and alkoxy groups, for example cyanothienyl and formylpyrrolyl.

The expression "heterocarbon group" denotes a group containing at least one heteroatom selected from O and N with at least one carbon-heteroatom multiple bond at the C-1 position, the group being bonded via the C-1 atom. The group is essentially a functionality which can be bonded to an aromatic system via an addition or can be reduced with addition of a leaving group onto the C-1 atom. Typical heterocarbon groups are carboxylic acid groups and derivatives thereof, such as acid halides, amides and esters, and also nitrites.

The expression "salts" relates preferably to metal salts, especially alkali metal salts.

Hydrates and solvates of the compounds according to the invention are likewise included.

The compounds according to the invention of the formula (IIa) and (IV) and the compounds of the formula (I) possess chiral centers and may be present in any stereoisomeric form. The present invention encompasses all stereoisomeric forms, or mixtures thereof, of a compound according to the invention or desired compound, it being known how the optically active forms can be obtained (for example by separating the racemic form by recrystallization methods, by synthesis from optically active starting materials, by chiral synthesis or by chromatographic separation by means of a chiral stationary phase).

The compounds according to the invention of the formulae (IIa), (IIb) and (IV) can advantageously be used to prepare octenoic acid derivatives, more preferably in the process according to the invention.

The process according to the invention is based essentially on the separate preparation first of the side chain of the compound of the general formula (I) which contains two chiral centers, taking account of the symmetry element present therein, which significantly simplifies the overall synthesis and can considerably reduce the number of reaction steps. In a second stage, this symmetrical chiral side chain precursor can be coupled to a suitable aromatic unit to obtain the desired chiral octenoic acid of the formula (I) within few reaction steps.

DETAILED DESCRIPTION OF THE INVENTION

Figure 1:
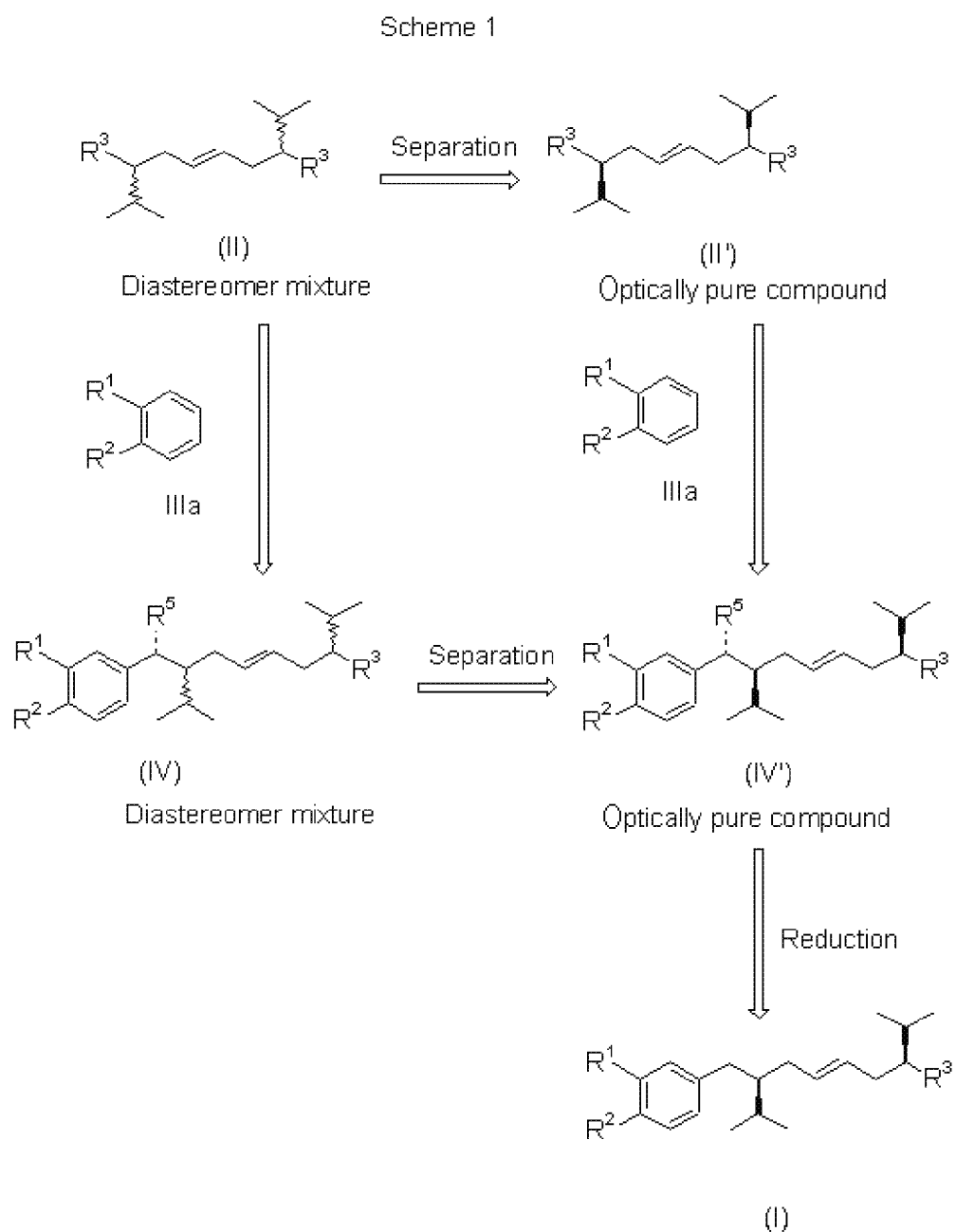
FIG. 1 is an illustration of Scheme 1 showing synthesis route A) first addition of the compound of the formula (III) to obtain a compound of the formula (IV) and subsequent reduction of the compound of the formula (IV).
Figure 2:
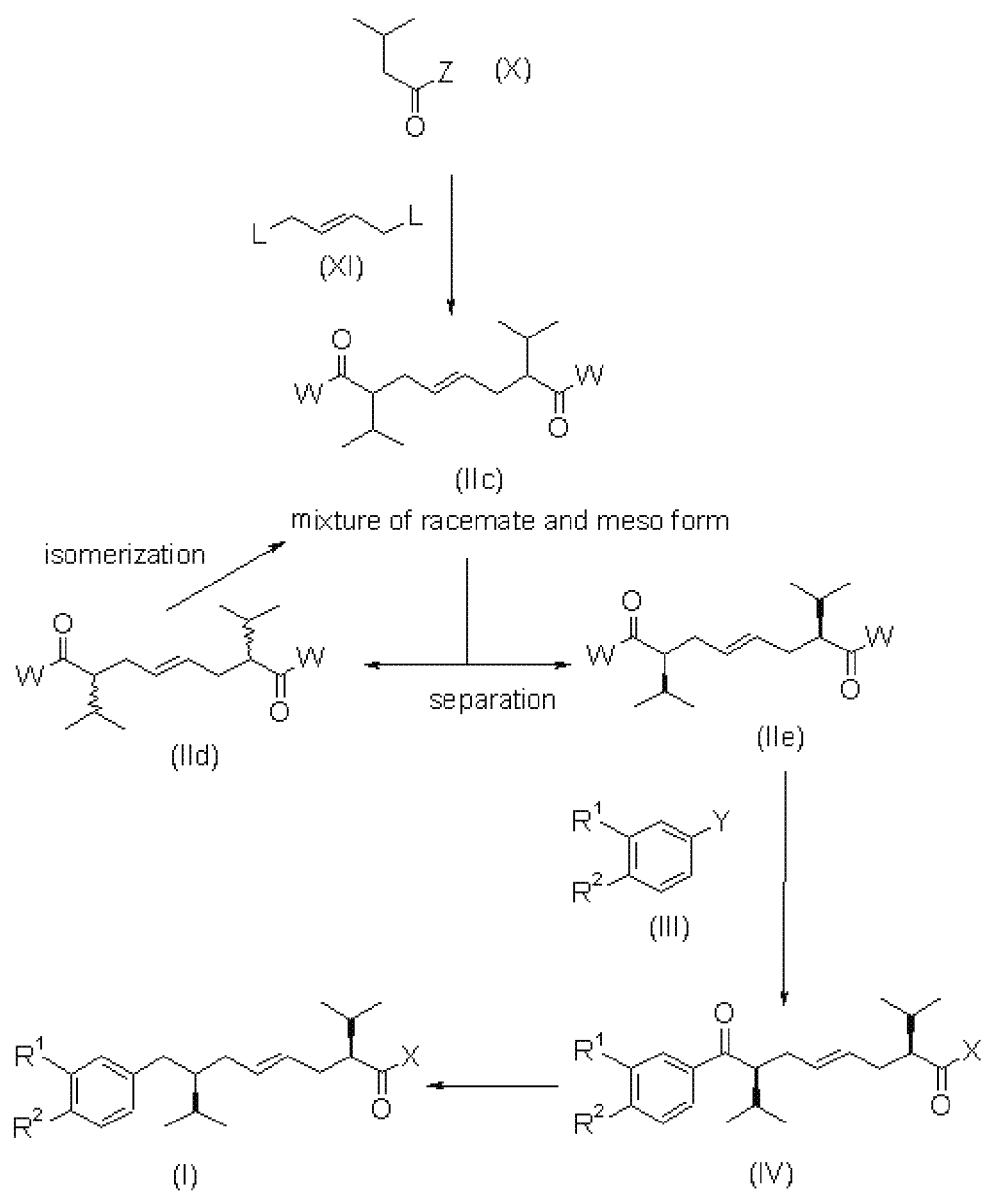
FIG. 2 is an illustration of Scheme 1a showing the intermediate of formula (IV) being obtained by addition of a compound of formula (III) onto a chiral compound of formula (IIe) which leads to the compound of formula (I).
Figure 3:
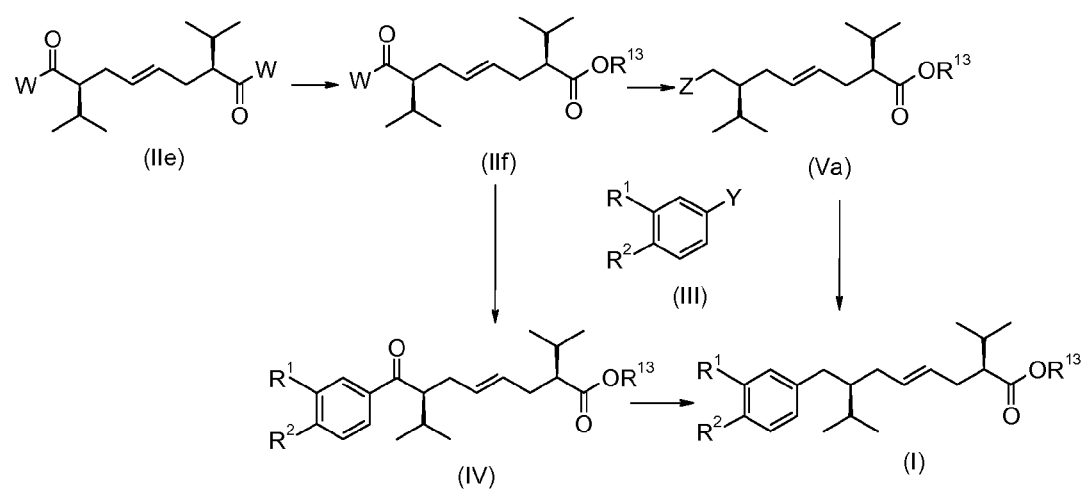
FIG. 3 is an illustration of Scheme 2 showing the intermediate of formula (IV) being obtained by addition of a compound of formula (III) on a chiral compound of formula (IIf) which leads to the compound of formula (I). Also, showing the compound of formula (I) being obtained directly by a coupling reaction of the chiral compound of formula (Va) with a compound of formula (III).
Figure 4:
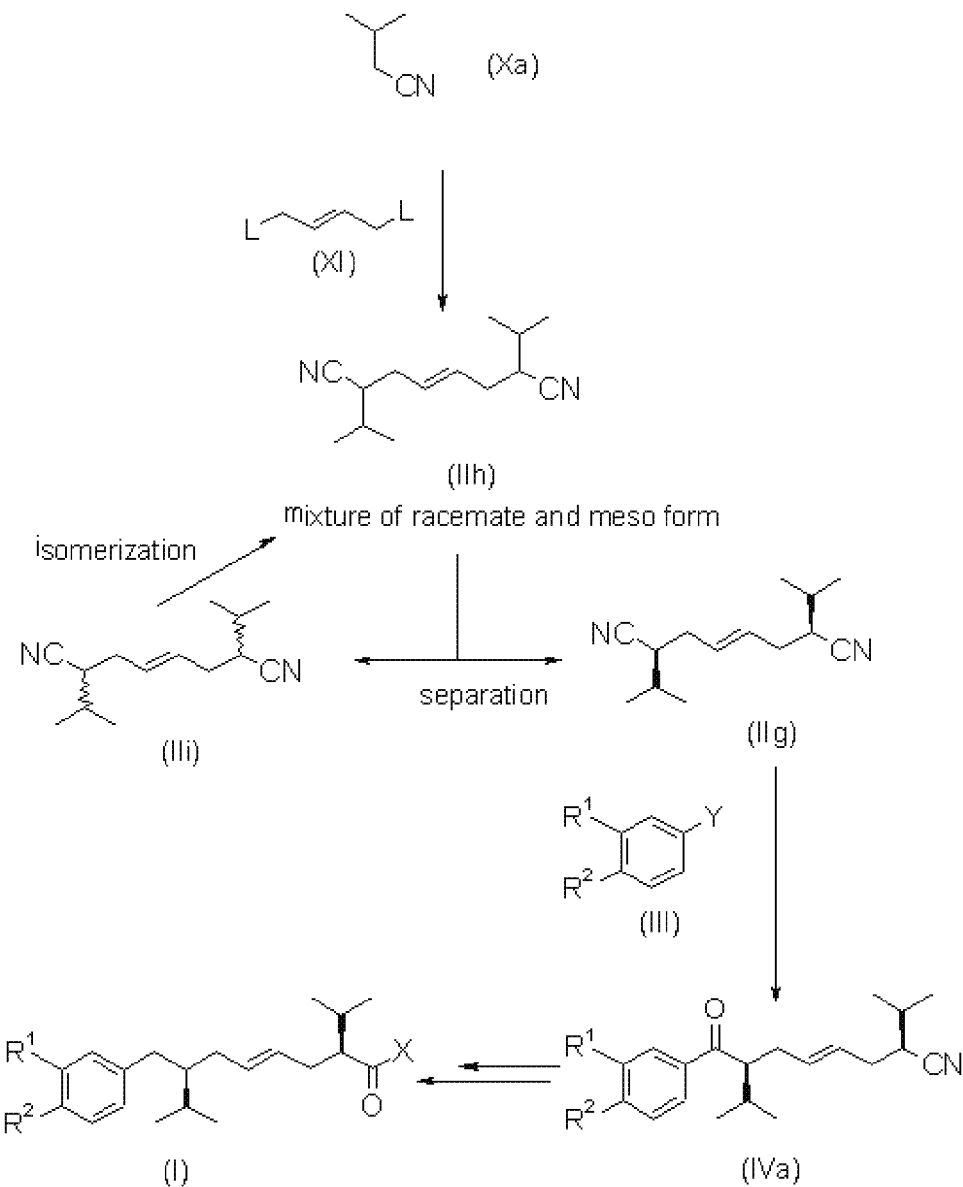
FIG. 4 is an illustration of Scheme 3 showing the preparation of the compound of formula (I) via nitrile compounds of formula (IV).
Figure 5:
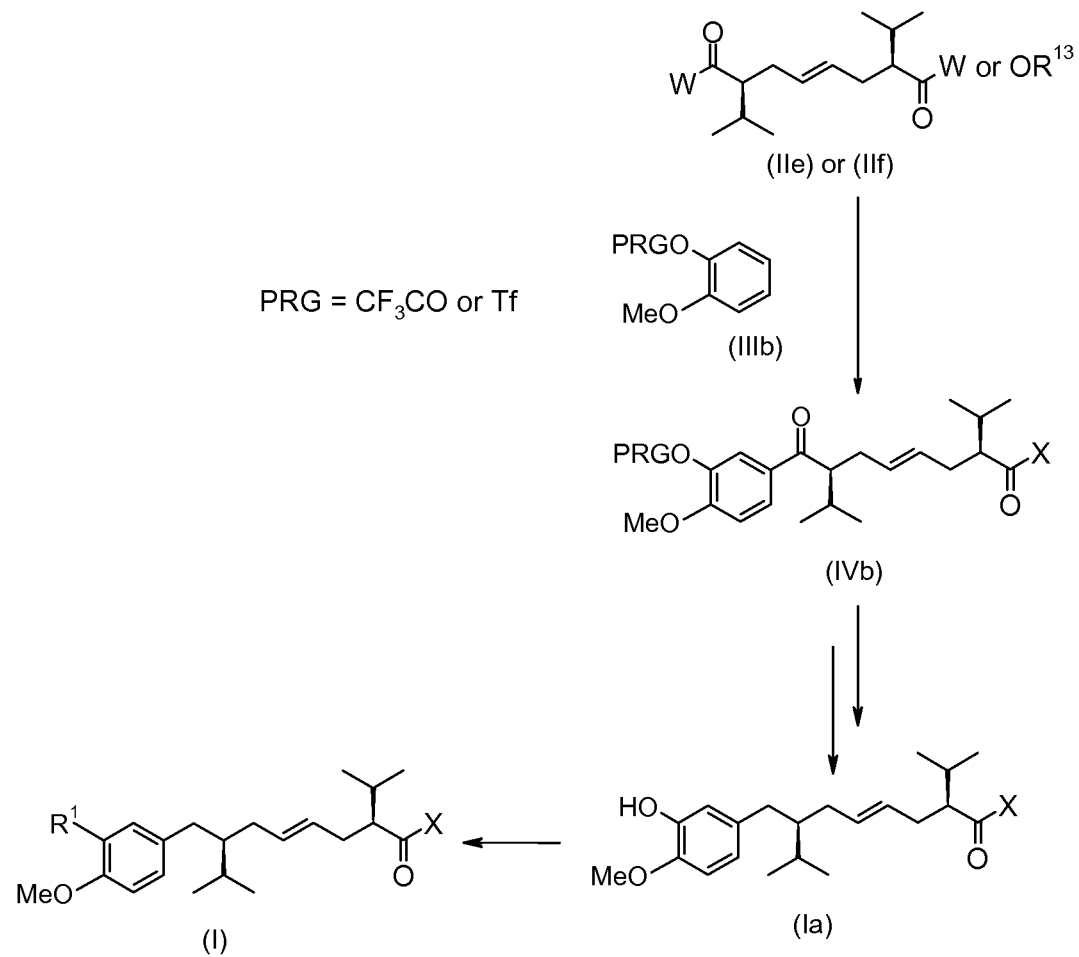
FIG. 5 is an illustration of Scheme 4 showing the compound of formula (I) being obtained by alkylating the phenolic group of a compound of formula (Ia) in the presence of a base, wherein formula (Ia) was prepared according to Scheme 3.

The present invention and additional embodiments of the invention are described in detail hereinafter in the detailed description.

According to the invention, the compound of the general formula (I) can be obtained proceeding from a compound of the general formula (II) by two alternative routes, i.e.
A) either by a first addition of the compound of the formula (III) to obtain a compound of the formula (IV) and subsequent reduction of the compound of the formula (IV) or
B) by reduction of the compound of the formula (II) to obtain a compound (V) and subsequent addition of the compound of the formula (III).

In scheme 1, synthesis route A) is illustrated in detail hereinafter with reference to the preferred embodiment with an additional isomer separation, which affords the desired product of the formula (I) in isomerically pure form. Proceeding from a compound of the formula (II), addition of a compound of the formula (IIIa) leads to an 8-oxooctenoic acid (IV) which has, in the 1 position, i.e. in the benzyl position, the $R^5$ radical bonded via a single or double bond. In the present case, $R^5$ is, by way of example, a keto group which is reduced in one or more steps in the subsequent reaction. $R^5$ might equally be a likewise reducible hydroxyl group. As shown, the intermediate of the formula (IV) can be obtained by two alternative routes. For instance, proceeding from a mixture of the stereoisomers of the compound of the formula (II), either first an isomer separation and then the addition of the compound of the formula (IIIa) or first the addition and then an enantiomer separation can be undertaken. It is obvious that the reaction can also be carried out with different isomers than those specified of the compounds of the formulae (II) and (IV) or mixtures thereof, which leads to corresponding isomers and/or mixtures of the compound of the formula (I).

Preferably, $R^1$ and $R^2$ are each independently hydroxyl or branched or unbranched lower alkoxy having from 1 to five carbon atoms, such as methoxy, ethoxy, n- and i-propoxy, n-, i- and t-butoxy or pentoxy, aryloxy such as phenyloxy, naphthyloxy or derivatives thereof, or benzyloxy or branched or unbranched alkoxyalkoxy having in each case from 1 to 5, preferably from 1 to 2 carbon atoms in the alkoxy group, such as 1-methoxymethoxy, 1-methoxy-2-ethoxy, 1-methoxy-3-propoxy, 1-methoxy-4-butoxy, etc.

The X radical is appropriately $O^-$, OH or a salt, such as OM in which M is an alkali metal or an equivalent of an alkaline earth metal. Further suitable meanings of X are $OR^{11}$ in which $R^{11}$ is alkyl, preferably unbranched or branched lower alkyl having from 1 to 5 carbon atoms, aryl such as phenyl, naphthyl or alkoxy derivatives thereof, benzyl, diphenylmethyl, trityl or trialkylsilyl or $NR^4R^5$ in which $R^4$ and $R^5$ are each independently alkyl, preferably unbranched or branched lower alkyl having from 1 to 5 carbon atoms, or benzyl or trialkylsilyl. $R^4$ and $R^5$ may, together with the nitrogen, form a typically 5- to 6-membered heterocyclic ring system such as pyrrole, imidazole and the like. X may likewise be a protecting or activating group customary for carboxylic acids, such as Weinreb amide, preferably N-alkyl-O-alkyl, in which alkyl is preferably straight-chain or branched lower alkyl having from 1 to 5 carbon atoms, or the nitrogen is part of a heterocyclic ring system such as pyrrole, imidazole and the like.

The reduction stage of the keto function can be carried out in one or more steps. The reductive removal of the oxygen function in the benzyl position to the corresponding hydrocarbon can be effected via various known methods which do not simultaneously reduce the double bond present in the aliphatic chain (see. J. March, John Wiley & Sons, NY, 1992, Advanced Organic Chemistry, p. 1209-1211). In the suitable methods, the reaction can be carried out without solvent, or in polar or nonpolar, protic or aprotic solvents, preferably in aprotic solvents such as chlorinated hydrocarbons or hydrocarbons, preferably at temperatures between −20° C. and reflux temperature of the solvent.

Preferably, trialkylsilane can be used in the presence of acids, preferably trifluoromethanesulfonic acid or trifluoroacetic acid, or Lewis acids, preferably $BF_3$.etherate, $ZnCl_2$, $AlCl_3$, $TiCl_4$.

The reduction can also be carried out in several steps when the 8-oxo group of the compound of the formula (IV) is first reduced with, for example, metal hydrides to give the corresponding 8-hydroxy compound which, in turn, thereafter, is either reduced directly to the desired compound of the formula (I) or, after preceding conversion of the hydroxyl group to a suitable leaving group, preferably mesylate, tosylate, etc., and subsequent reduction, is converted to the desired compound of the formula (I).

Schemes 1a and 2 show further advantageous embodiments of the process according to the invention. The intermediate of the formula (IV) in which the $R^1$, $R^2$ and X radicals are each as defined above can be obtained by addition of a compound of the formula (III)

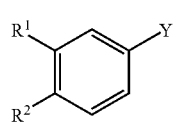

in which $R^1$ and $R^2$ are each as defined for the compound of the formula (IV), and Y is various metals such as alkali metals or metal halide, metal alkoxide or metal carboxylate, in which the metal may be Mg, Al, B, Mn, Cu, Cd, Zn and Sn, onto a) a chiral compound of the formula (IIe)

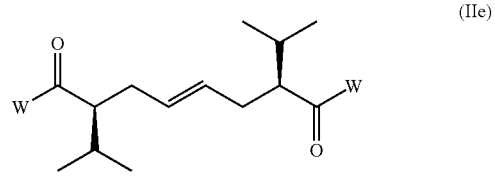

in which

W is in each case independently, appropriately, $O^-$, OH or a salt such as OM in which M is an alkali metal or an equivalent of an alkaline earth metal, or is halogen, such as Cl, Br, I, preferably Cl, or is $OCOR^{12}$ in which $R^{12}$ is branched lower alkyl having from 1 to 5 carbon atoms, preferably pivaloyl, or $OCOCF_3$, $OSO_2CH_3$ or $OSO_2CF_3$ or is $OR^{11}$ in which $R^{11}$ is preferably unbranched or branched lower alkyl having from 1 to 5 carbon atoms, aryl, benzyl or trialkylsilyl, or $NR^4R^5$ in which $R^4$ and $R^5$ are each independently preferably unbranched or branched lower alkyl having from 1 to 5 carbon atoms or benzyl or trialkylsilyl, or $R^4$ and $R^5$ may, together with the nitrogen, form a typically 5- to 6-membered heterocyclic ring system such as pyrrole, imidazole and the like, W may likewise be a protecting or activating group customary for carboxylic acids, such as Weinreb amide, preferably N-alkyl-O-alkyl, in which alkyl is preferably unbranched or branched lower alkyl having from 1 to 5 carbon atoms, or the nitrogen is part of a heterocyclic ring system such as pyrrole, imidazole and the like, or b) onto a chiral compound of the formula (IIf)

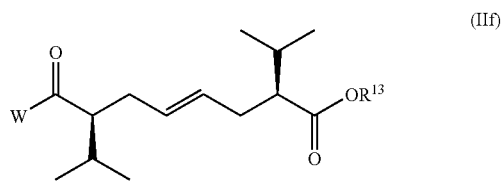

in which

W is advantageously hydrogen or halogen, such as Cl, Br, I, preferably Cl, or is $OCOR^{12}$ in which $R^{12}$ is branched lower alkyl having from 1 to 5 carbon atoms, preferably pivaloyl, or $OCOCF_3$, $OSO_2CH_3$ or $OSO_2CF_3$ or is a protecting or activating group customary for carboxylic acids, such as Weinreb amide, preferably N-alkyl-O-alkyl, in which alkyl is preferably unbranched or branched lower alkyl having from 1 to 5 carbon atoms, or the nitrogen is part of a heterocyclic ring system, such as pyrrole, imidazole and the like, and $R^{13}$ is branched or unbranched lower alkyl having from 1 to 5 carbon atoms, or is benzyl or trialkylsilyl, followed by a subsequent manipulation of the functional group depending on the definition of the X radical of the compound of the formula (IV). It is obvious that the reaction can also be carried out with isomers other than those specified above of the compounds of the formulae (IIe), (IIf) and (IV) or mixtures thereof, which leads to corresponding isomers and/or mixtures of the compound of the formula (I).

The precursor of the organometallic compound of the formula (III), preferably 4-bromo-2-(3-methoxypropyl-1-oxy)-1-methoxybenzene, can be prepared either by the process as described in documents EP 678503, WO 03/103653 or WO 04/089915, or alternatively via a process in which guaiacol is acylated, preferably benzoylated, and subsequently brominated (see Synthesis (5), 559, 1997 or THL 41(6), 811, 2000). After removal of the protective acyl group, preferably benzyl group, the free phenol is treated with 3-halopropanol, preferably with 3-chloropropanol, and then the free hydroxyl group in the side chain is methylated with MeI or dimethyl sulfate in the presence of a base, preferably an alkali metal hydride, alkali metal amide or tert-aliphatic amine, such as triethylamine and the like.

The organometallic reagent of the formula (III) can be prepared from the abovementioned aromatic halide, preferably bromide, either by direct metallation with metals such as alkali metals or Mg, Al, B, Mn, Zn, Sn, Cd or Cu, or via transmetallation of an initially formed alkali metal compound in which Y is preferably Li, by addition of another metal halide, preferably magnesium halide, (see EP 678503).

Preference is given to using a Grignard reagent of the formula (III) in which Y is MgCl or MgBr, which is obtained from the corresponding aromatic bromide by metallation with BuLi and subsequent transmetallation with Mg(II) bromide or Mg(II) chloride, for example in THF.

A compound of the formula (III) in which Y is MgCl*LiCl is obtainable, for example, by reacting the aromatic halide (III with Y=halogen), preferably the bromide, with an $^i$PrMg Cl*LiCl complex, as described by Knochel et al. in EP 1582523 A1 or in Angew. Chem. Int. Ed. 2004, 43, 3333-3336.

The organometallic compound of the formula (III) is then reacted in aprotic solvent with the compound of the formula (IIe) in which W is OH or OM (acid or salts thereof, OR (ester), OCOR$^{12}$ or halogen. Preference is given to using the acid chloride or bromide for the reaction with the compound of the formula (III) in the absence or in the presence of catalytic or stoichiometric amounts of Cu(I) or Cu(II) salts, such as Cu(I) bromide or Cu(I) chloride.

The reaction temperature may be between −78° C. and reflux temperature of the solvent; preference is given to THF at 0° C. or RT. The selection of the aprotic solvent is uncritical. The ratio of the compounds of the formula (III) to (IIe) may be between 0.1 and 2.0, preferably between 0.3 and the stoichiometric ratio.

In the case of use of the compound of the formula (IIf) in which W is hydrogen or halogen, preferably Cl or Br, a higher yield can be achieved, since the aldehyde or acid chloride leads selectively to the monoaddition product of the compound of the formula (IV).

As likewise shown in scheme 2, a compound of the formula (I) in which R$^1$ and R$^2$ are each independently hydroxyl, unbranched or branched lower alkoxy having from 1 to 5 carbon atoms, aryloxy, arylalkyloxy or benzyloxy, and R$^3$ is COOR$^{13}$, and R$^{13}$ is branched or unbranched lower alkyl having from 1 to 5 carbon atoms or is benzyl or trialkylsilyl, can be obtained directly by a coupling reaction of the chiral compound of the formula (Va)

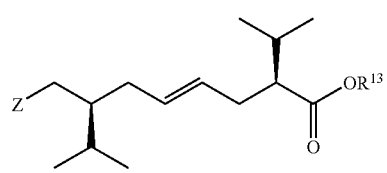

(Va)

in which
Z is halogen, preferably iodine, or another customary leaving group, such as mesylate, tosylate or triflate, and
R$^{13}$ is branched or unbranched lower alkyl having from 1 to 5 carbon atoms, or is benzyl or trialkylsilyl,
with a compound of the formula (III)

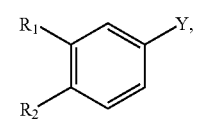

(III)

in which R$^1$ and R$^2$ are each as defined above for the compound of the formula (I) and Y represents various metals such as alkali metals or metal halides, in which the metal may be Mg, Al, B, Mn, Cu and Zn.

The coupling of the compounds of the formula (III) and (Va) can preferably be catalyzed by transition metals such as various Pd(0) complexes or Pd(II) salts, for example PdCl$_2$.acetonitrile complex, Pd(II) acetate, Pd(PPh$_3$)$_4$ or Pd(dba), etc., in protic or aprotic polar solvents at a reaction temperature of from RT to reflux temperature of the solvent. The chiral compound of the formula (Va) can be obtained easily from the chiral compound of the formula (IIf) by selective reduction of the free carboxylic acid with, for example, diborane and the like.

EP 0678514 and U.S. Pat. No. 5,606,078 describe the stereoselective alkylation of chiral isovaleramides with Evans auxiliaries to obtain trans-1,8-bis[4(S)-benzyl-2-oxo-oxazolidin-3-yl]-2(S)-7(S)-diisopropyloct-4-ene-1,8-dione. However, object of the present invention is specifically the avoidance of use of expensive chiral auxiliaries which, coupled to isovaleric acid, would probably lead to stereoselective chiral precursors for preparing compounds of the formula (IIe). The compounds of the formula (II), especially of the formula (IIe) and (IIf), in which W is as defined above, are accordingly novel intermediates. According to the invention, the compound of the formula (II) can be used as an easily obtainable stereoisomeric mixture which is then subjected to an enantiomer separation if required.

As shown in scheme 1a, the chiral compound of the formula (IIe)

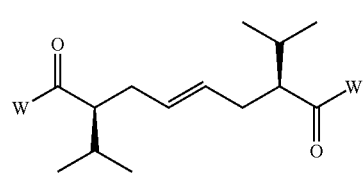

(IIe)

in which
W is as defined above,
can be obtained by the following steps:

a) alkylation of the deprotonated isovaleric acid of the formula (X)

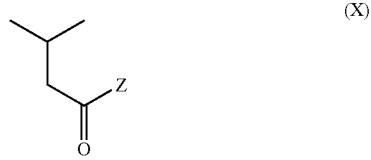

in which
Z is OH or OM in which M is an alkali metal, an equivalent of an alkaline earth metal or —O⁻, or is $OR^{11}$ in which $R^{11}$ is preferably unbranched or branched lower alkyl having from 1 to 5 carbon atoms, aryl, benzyl or trialkylsilyl, or $NR^4R^5$ in which $R^4$ and $R^5$ are each independently unbranched or branched lower alkyl having from 1 to 5 carbon atoms, or benzyl or trialkylsilyl,
with a compound of the formula (XI)

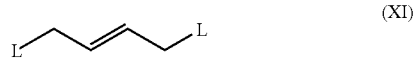

in which
L is a customary leaving group, such as halogen, preferably Cl or Br, or mesylate, tosylate or triflate,
b) optional hydrolysis of the ester or amide group if the ester or the amide of isovaleric acid has been used in the alkylation step a),
c) separation of the resulting diastereomeric acids of the formula (IIe) and subsequent enantiomer separation (resolution) of the racemic acid of the formula (IIe), including epimerization of the undesired isomer,
d) conversion of the chiral acid of the formula (IIe) to the corresponding acid chloride, ester, amide and the like depending on the W radical by known standard methods.

The compound of the formula (IIe) may also be present as another enantiomer or racemate, or in meso form.

The alkylation of isovaleric acid or derivatives thereof, such as esters or amides, can be carried out in aprotic solvents, preferably THF, toluene or ether, after an initial deprotonation of the compound (X) with a strong base, such as alkali metal hydrides or alkali metal amides, preferably lithium dialkylamides such as LDA or LHMDS, at from −78° C. to 0° C. or even at RT. The deprotonated compound (X) is then treated with 0.5 equivalent of the compound of the formula (XI) at from −78° C. to RT, preferably at 0° C. The untreated mixture comprises an essentially equimolar mixture of the two possible diastereomers, which, in the case of use of the ester or amide, is hydrolyzed to the free acid (IIe).

Alternatively, instead of the isovaleric acid derivatives, the corresponding isopropyl malonate or the isopropyl derivative of Meldrum's acid can be used. In this case, not only strong bases need be used, which also allows customary phase transfer catalysts or organic amides to be used for the alkylation of the compound (XI). Preference is given to using metal hydrides or amides, especially NaH, as the base in aprotic solvents, such as THF, toluene or ethers, which leads to particularly high yields. After the alkylation, the malonates are hydrolyzed, followed by a decarboxylation to obtain a mixture of diastereomeric acids of the formula (IIe) in which W is OH or OM in which M is an alkali metal or the equivalent of an alkaline earth metal or —O⁻.

The removal of the desired isomer from the mixture of the diastereomeric diacid (IIe), which is to be undertaken if appropriate, can be effected in a one-stage or two-stage process using different separation techniques, such as chromatography or crystallization processes. The meso acids and racemic acids are preferably first separated by means of a kinetically controlled crystallization from a supersaturated solution in an organic solvent or a solvent mixture, preferably ester, e.g. isopropyl acetate. In a second step, the desired enantiomer is separated by enantiomer separation of the racemic diacid (IIe) via a diastereomeric salt with various chiral amines or complexing agents, preferably amino acids or derivatives thereof, especially phenylalaminol, or arylalkylamines such as 1-naphthylethylamine or phenylethylamine derivatives, preferably 1-(4-methylphenyl)ethylamine or ephedrine or alkaloids such as cinchonine or other chiral amines such as 3-aminopentanenitrile or 1,2-diaminocyclohexane or 2-amino-1-butanol or (1R,2S)-1-amino-2-indanol or benzylaminobutanol. The diastereomerically enriched crystals or mother solutions can be purified by recrystallization to obtain the pure diastereomeric salt, from which the enantiomerically pure diacid (IIe) is obtained. This salt splitting can be carried out using standard methods, such as extraction from an acidic aqueous solution with an organic solvent, preferably esters or ethers, such as tert-butyl methyl ether, or using ion exchange resins. The undesired isomer or mixtures thereof can be isomerized and recycled into the separation process. The isomerization can be effected by heating the compound (IIe) or derivatives thereof, preferably esters, acid chlorides or acid anhydrides, under basic or acidic conditions. For example, the epimerization of the meso-diacid (IIe) can be carried out under reflux in acetic anhydride in the presence of potassium acetate, which leads to a 1:1 mixture of the meso-diacid and racemic diacid (IIe).

The chiral compound of the formula (IIf)

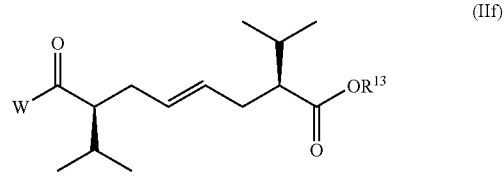

in which
W and $R^{13}$ are each as defined above,
can be obtained easily from the chiral compound (IIe) in which W is OH by the following steps:
a1) selective monoesterification, as described in J. Chem. Soc., Perkin Trans 1, 1999, p. 3023-27, to obtain the monoester,
or
a2) selective hydrolysis of one of the two ester functions of a diester compound (compound IIf with W=$OR^{13}$)—which is itself obtainable easily by acidic esterification from the diacid (compound IIe with W=OH) or by reacting the acid chloride (IIe with W=Cl) with an alcohol—under basic conditions, for example with alkali metal or alkaline earth metal hydroxides, preferably NaOH, KOH or Ba(OH)₂ (see *Organic Syntheses*, Coll. Vol. 4, p. 635 (1963); Vol. 38, p. 55 (1958); and *J. Med. Chem.* 2004, 47, 2318-2325) to obtain the monoester; and further reaction of the resulting monoester, as follows:
b1) conversion of the free carboxyl function to the acid chloride or bromide by means of thionyl chloride or bromide or oxalyl chloride or bromide,
or
b2) conversion of the free carboxyl function to the mixed anhydride by means of the corresponding acid chloride or anhydride, trifluoromethanesulfonic anhydride, trifluoroacetic anhydride or mesyl chloride,
or
b3) conversion of the free carboxyl function to aldehyde by reduction with diborane or by hydrogenation of the acid chloride.

The compound of the formula (IIf) may also be present as another enantiomer, racemate or, if possible, in meso form or as an isomer mixture.

A further embodiment of the process according to the invention relates to the preparation of the compound of the formula (I) via nitrile compounds of the formula (IV), as shown in scheme 3.

The compound of the formula (IVa)

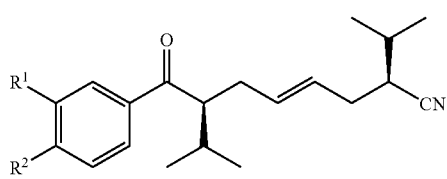

(IVa)

in which the R¹, R² radicals are each as defined above, can be obtained by addition of a compound of the formula (III)

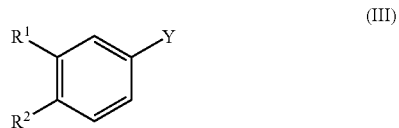

(III)

in which R¹ and R² are each as defined for the compound of the formula (IVa) and Y represents various metals such as alkali metals or metal halide, metal alkoxide or metal carboxylate, in which the metal may be Mg, Al, B, Mn, Cu, Cd, Zn and Sn,
onto a chiral compound of the formula (IIg)

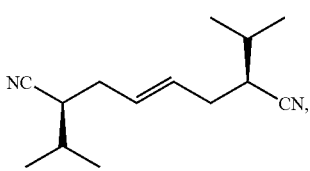

(IIg)

the invention not being restricted to the stereochemical forms of the compounds of the formula (IIg) and (IVa) shown, but rather these compounds may also be present as another enantiomer, racemate or, for (IIg), also in meso form or as an isomer mixture.

The chiral compound of the formula (IIg) can be obtained by the following steps:
a) alkylation of the deprotonated isovaleronitrile of the formula (Xa)

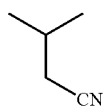

(Xa)

with a compound of the formula (XI)

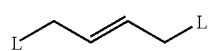

(XI)

in which
L is a customary leaving group, such as halogen, preferably Cl or Br, or mesylate, tosylate or triflate, etc.,
b) separation of the resulting diastereomeric nitrile and subsequent enantiomer separation of the racemic nitrile.

The compound of the formula (IIg) may also be present as another enantiomer, racemate or in meso form, or a mixture thereof.

The alkylation of the isovaleronitrile can be carried out in aprotic solvents, preferably THF, toluene or ether, after an initial deprotonation of the compound (Xa) with a strong base, such as alkali metal hydrides or alkali metal amides, preferably lithium dialkylamides such as LDA or LHMDS, at from −78° C. to 0° C. or even at RT. The deprotonated nitrile (Xa) is then treated with 0.5 equivalent of the compound of the formula (XI) at from −78° C. to RT, preferably at 0° C. The untreated mixture comprises an essentially equimolar mixture of the two possible diastereomers, which are subsequently separated.

A further preferred variant of the process according to the invention for preparing the compound of the formula (I) in which
R¹ is 1-methoxy-3-propoxy,
R² is methoxy and
R³ is COOR⁶ in which R⁶ is H or M, in which M is an alkali metal, an equivalent of an alkaline earth metal or unbranched or branched lower alkyl having from 1 to 5 carbon atoms, benzyl or trialkylsilyl, is shown in scheme 4.

The compound of the formula (I) is obtainable by alkylating the phenolic group of a compound of the formula (Ia)

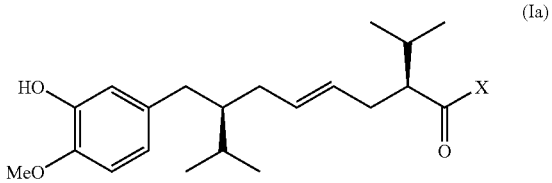

(Ia)

in which C(O)X is as defined above for R³
with 3-methoxy-1-propyl halide, preferably chloride or bromide, in the presence of a base.

The compounds of the formula (Ia) can be prepared according to scheme 3 by Friedel-Crafts reaction of a compound of the formula (IIe) or (IIf) in which W is halogen, preferably Cl or Br, or OCOR¹² in which R¹² is branched lower alkyl having from 1 to 5 carbon atoms, preferably pivaloyl, or OCOCF₃, OSO₂CH₃ or OSO₂CF₃, and R¹³ is branched or unbranched lower alkyl having from 1 to 5 carbon atoms or is benzyl,
with a compound of the formula (IIIb)

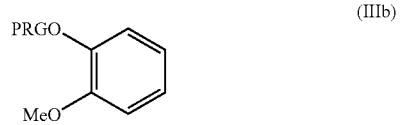

(IIIb)

in which PRG is a protecting group such as trifluoroacetate or trifluoromethanesulfonate,
to obtain a compound of the formula (IVb)

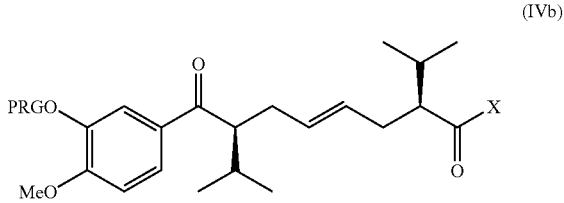

(IVb)

in which C(O)X is as defined above for R³.

The hydrolytic removal of the leaving group PRG to obtain the free hydroxyl function can alternatively be effected before or after the reduction of the 8-oxo group.

The reaction can be carried out in aprotic solvents customary for Friedel-Crafts reactions, preferably chlorinated hydrocarbons such as methylene chloride, dichloroethane, or hydrocarbons, preferably hexane or heptane. The Lewis acids used as the catalyst may be $BF_3$-etherate or metal halides, preferably aluminum halides or triflates, zinc halides or triflates or bismuth halides or triflates. The reaction temperature may be between room temperature and reflux temperature of the solvent.

The 8-oxo group can be reduced by the processes described above.

EXAMPLES

Example 1 trans-2,7-Diisopropyloct-4-ene-1,8-dionic acid

To a cooled (−78° C.) solution of diisopropylamine (58.7 g; 580 mmol) in dry THF (300 ml) was slowly added n-BuLi (362 ml, 1.6 M in hexane). After stirring at −78° C. for 10 min, isovaleric acid (29.5 g, 290 mmol) was slowly added dropwise. On completion of addition, the reaction mixture was warmed to 0° C. over the course of 1 h, and trans-1,4-dichloro-2-butene (17.3 g, 138 mmol) was added slowly at 0° C. On completion of addition, the reaction mixture was stirred at RT for 16 h. The reaction mixture was then added to water (400 ml). The water layer was extracted 3× with t-butyl methyl ether, and the aqueous phase was subsequently acidified with concentrated HCl. The acidic water layer was extracted 3× with t-butyl methyl ether, dried over $MgSO_4$ and concentrated under reduced pressure to obtain trans-2,7-diisopropyloct-4-enedionic acid as a white powder (36 g; meso/rac: 53:47; purity (HPLC): 95%). Recrystallization from methylcyclohexane gave trans-2,7-diisopropyloct-4-enedionic acid (28.3 g; 80%) as white crystals.

$^1$H NMR ($CDCl_3$, 400 MHz): δ=0.95 (m, 12H); 1.86 (m, 2H); 2.22 (m, 6H); 5.45/5.50 (2 m, 2H); 10.4 (bs, 2H).
$^{13}$C NMR ($CDCl_3$, 100.6 MHz): δ=19.90; 20.51; 20.56; 30.04; 30.22; 31.88; 32.32; 52.81; 52.86; 129.40; 129.44; 180.25; 180.59;
MS: (Cl, ammonia): m/z=274.2 [$M+NH_4^+$]; 256.2 [$M^+$].

Example 2

Diastereomer separation: (2R,7S)-trans-2,7-diisopropyloct-4-ene-1,8-dionic acid (IIe in which W═OH) and (2R,7R)-trans-2,7-diisopropyloct-4-ene-1,8-dionic acid and (2S,7S)-trans-2,7-diisopropyloct-4-ene-1,8-dionic acid A mixture of meso and racemic trans-2,7-diisopropyloct-4-ene-1,8-dionic acid (17.7 g; meso/rac=49:51) was dissolved in hot isopropyl acetate (16 g) and cooled to RT within 1 h. The spontaneously crystallizing material was filtered off and washed 3× with hexane (10 g) to obtain rac-trans-2,7-diisopropyloct-4-enedionic acid (3.8 g; meso/rac=4:96). Recrystallization of this material from isopropyl acetate gave pure racemic diacid (IIe) (purity>99%). Acetone (20 g) was added to the mother solution and the mixture was stirred for 30 min. The crystals were filtered off and washed with acetone to obtain the meso-diacid (IIe) (3.3 g, meso/rac=87:13). Evaporating off the mother solution gave a mixture of meso and racemic diacid (10.3 g, meso/rac=59:41), which was used again for the separation.

meso: (2R,7S)-trans-2,7-diisopropyloct-4-ene-1,8-dionic acid, melting point: 108° C.

$^1$H NMR ($CDCl_3$, 400 MHz): δ=0.95 (m, 12H); 1.86 (m, 2H); 2.22 (m, 6H); 5.55 (m, 2H); 9.9 (bs, 2H).
$^{13}$C NMR ($CDCl_3$, 100.6 MHz): δ=19.90; 20.51; 30.04; 31.88; 52.81; 129.43; 180.26.

rac-trans-2,7-diisopropyloct-4-ene-1,8-dionic acid, melting point: 108.5° C.

$^1$H NMR ($CDCl_3$, 400 MHz): δ=0.95 (m, 12H); 1.86 (m, 2H); 2.22 (m, 6H); 5.45 (m, 2H); 10.4 (bs, 2H).
$^{13}$C NMR ($CDCl_3$, 100.6 MHz): δ=20.04; 20.72; 30.41; 32.45; 52.99; 129.58; 180.50.

Example 3

Enantiomer separation of the racemic mixture: (2R, 7R)-trans-2,7-diisopropyloct-4-ene-1,8-dionic acid and (2S,7S)-trans-2,7-diisopropyloct-4-ene-1,8-dionic acid 3a) Enantiomer Separation with (+)-ephedrine To a solution of racemic trans-2,7-diisopropyloct-4-ene-1,8-dionic acid (10 g, 39 mmol) in acetone (80 ml) was added (+)-ephedrine (10.2 g, 61.7 mmol). After the mixture had been stirred at RT for 1 h, the crystals were filtered off and washed with hexane to obtain (+)-ephedrine*(−)-(2S,7S)-trans-2,7-diisopropyloct-4-ene-1,8-dionic acid with a diastereomer ratio of 82:18 (HPLC). Recrystallization from acetone gave 4.9 g of the (+)-ephedrine*(−)-(2S,7S)-trans-2, 7-diisopropyloct-4-ene-1,8-dionic acid with a diastereomer ratio of 98:2 (HPLC).

The other enantiomer, the (+)-(2R,7R)-trans-2,7-diisopropyloct-4-ene-1,8-dionic acid, can be isolated from the mother solution.

Salt splitting: The (+)-ephedrine*(−)-(2S,7S)-trans-2,7-diisopropyloct-4-ene-1,8-dionic acid (4.9 g) was treated with tert-butyl methyl ether and aqueous 1N NaOH. The water layer was extracted 3× with tert-butyl methyl ether and then acidified with concentrated HCl. The acidic water layer was extracted 3× with t-butyl methyl ether, dried over $MgSO_4$ and concentrated under reduced pressure to obtain (−)-(2S,7S)-trans-2,7-diisopropyloct-4-ene-1,8-dionic acid (2.2 g, 8.4 mmol) as a colorless solid which crystallized slowly.

(−)-(2S,7S)-trans-2,7-Diisopropyloct-4-ene-1,8-dionic acid, $[\alpha]_D$=−12.3 (c=1; acetone)

The determination of the absolute configuration was determined by means of X-ray structural analysis of crystals of the salt of (−)-(2S,7S)-trans-2,7-diisopropyloct-4-ene-1,8-dionic acid with S-1-(4-methylphenyl)ethylamine.

3b) Enantiomer Separation with L-phenylalaminol

To a solution of racemic trans-2,7-diisopropyloct-4-ene-1, 8-dionic acid (0.5 g, 2 mmol) in acetone (4 ml) was added L-phenylalaminol (0.46 g, 3 mmol). After the mixture had been stirred at RT for 1.5 h, the crystals were filtered off and washed with hexane to obtain 0.41 g (0.73 mmol) of L-phenylalaminol*(−)-(2S,7S)-trans-2,7-diisopropyloct-4-ene-1, 8-dionic acid. Recrystallization from acetone gave 0.24 g (0.42 mmol) of L-phenylalaminol*(−)-(2S,7S)-trans-2,7-diisopropyloct-4-ene-1,8-dionic acid with a diastereomer ratio of 98:2 (HPLC).

The other enantiomer, the (+)-(2R,7R)-trans-2,7-diisopropyloct-4-ene-1,8-dionic acid, can be isolated from the mother solution.

Salt splitting: The L-phenylalaminol*(−)-(2S,7S)-trans-2, 7-diisopropyloct-4-ene-1,8-dionic acid (0.24 g) was treated with tert-butyl methyl ether and aqueous 1N NaOH. The water layer was extracted 3× with tert-butyl methyl ether, then acidified with concentrated HCl and extracted another 3× with tert-butyl methyl ether. The organic layer of the acidic extraction was dried over MgSO$_4$ and concentrated under reduced pressure to obtain (−)-(2S,7S)-trans-2,7-diisopropyloct-4-ene-1,8-dionic acid (0.10 g, 0.39 mmol) as a colorless solid which crystallized slowly.

Example 4

Isomerization of meso-(2R,7S)-trans-2,7-diisopropyloct-4-ene-1,8-dionic acid and/or (2R,7R)-trans-2,7-diisopropyloct-4-ene-1,8-dionic acid Meso-(2R,7S)-trans-2,7-diisopropyloct-4-ene-1,8-dionic acid (1 g, 3.9 mmol) was dissolved in acetic anhydride (10 ml), and potassium acetate (40 mg, 0.4 mmol) was added. The mixture was heated under reflux for 36 h and the reaction mixture was added to water. The aqueous layer was extracted 3× with tert-butyl methyl ether and the organic layer was concentrated under reduced pressure. The residue was dissolved in aqueous 1N NaOH and stirred for 2 h. The solution was acidified with HCl and the aqueous layer was extracted 3× with tert-butyl methyl ether. The organic layer was dried over MgSO$_4$ and concentrated under reduced pressure to obtain trans-2,7-diisopropyloct-4-ene-1,8-dionic acid (1 g, 3.9 mmol, HPLC: meso/rac=1:1) as a yellow solid.

Analogously to this process, (2R,7R)-trans-2,7-diisopropyloct-4-ene-1,8-dionic acid or mixtures of (2R,7S) and (2R,7R)dionic acid were isomerized.

Example 5

(2S,7S)-trans-2,7-Diisopropyloct-4-ene-1,8-dionyl chloride (IIe with W=Cl)

To a solution of (2S,7S)-trans-2,7-diisopropyloct-4-enedionic acid (2.0 g; 7.8 mmol) in dichloromethane (20 ml) was added oxalyl chloride (2.7 ml; 31.5 mmol), and the solution was stirred at RT for 16 h. The solution was concentrated under reduced pressure, evaporated off 2× with methylcyclohexane and dried under reduced pressure to obtain (2S,7S)-trans-2,7-diisopropyloct-4-ene-1,8-dionyl chloride as a colorless oil (2.3 g; 7.8 mmol), which was used without purification in the next stage.

Example 6

(2S,7S)-trans-2-Isopropyl-7-[4-methoxy-3-(3-methoxypropoxy)benzoyl]-8-methyl-non-4-enoic acid (IV with R$^1$=3-methoxypropoxy and R$^2$=methoxy and X=OH)

To a cooled (−78° C.) solution of 4-bromo-1-methoxy-2-(3-methoxypropyloxy)-benzene (III with R$^1$=1-methoxy-3-propoxy and R$^2$=methoxy and Y=Br) (2.4 g; 8.5 mmol) in dry THF (7 ml) was added dropwise n-BuLi (5.9 ml; 1.6 M in hexane), and the reaction mixture was stirred at −78° C. for 30 min. Thereafter, an MgCl$_2$ solution (20.1 ml; 0.505 M in THF) was added, and the reaction mixture was stirred at −78° C. for 20 min, warmed to RT and stirred for a further 30 min. This reaction mixture was added slowly to a cooled suspension of (2S,7S)-trans-2,7-diisopropyloct-4-enedionyl chloride (2.3 g; 7.8 mmol) and CuI (148 mg, 0.78 mmol) in dry THF (9 ml). The reaction mixture was stirred at −78° C. for 20 min, warmed to RT and stirred for a further 45 min. After adding water (40 ml), the reaction mixture was stirred for 1 h and then acidified with HCl. The aqueous layer was extracted 3× with tert-butyl methyl ether and the organic layer was dried over MgSO$_4$ and concentrated under reduced pressure. The crude residue was purified by column chromatography (eluent: hexane, tert-butyl methyl ether 3:1+0.5% acetic acid) to obtain the title compound (IV) (1.5 g; 3.45 mmol; 44% yield) as a pale yellow oil. (2S,7S)-trans-2,7-Diisopropyloct-4-enedionic acid (0.4 g; 1.6 mmol; 20%) was likewise isolated and used once again in a repeat step.

(2S,7S)-trans-2-Isopropyl-7-[4-methoxy-3-(3-methoxypropoxy)benzoyl]-8-methyl-non-4-enoic acid (IV with R$^1$=3-methoxypropoxy and R$^2$=methoxy and X=OH) TLC: (hexane:t-BME 1:1+0.5% acetic acid): Rf=0.3;

$^1$H NMR (CDCl$_3$, 400 MHz): δ=0.90 (m, 12H); 1.81 (m, 1H); 1.98-2.29 (m, 7H); 2.45 (m, 1H); 3.21 (m, 1H); 3.38 (s, 3H); 3.59 (dd, J$_1$=J$_2$=7 Hz, 2H); 3.92 (s, 3H); 4.18 (dd, J$_1$=J$_2$=7 Hz, 2H); 5.38 (m, 2H); 6.89 (d, J=9 Hz, 1H); 7.54 (m, 2H); 7.75 (bs, 1H).

$^{13}$C NMR (CDCl$_3$, 100.6 MHz): δ=19.68; 19.75; 20.02; 21.19; 29.39; 29.56; 29.69; 30.49; 32.20; 32.39; 52.30; 56.01; 58.54; 66.18; 69.26; 110.46; 112.50; 122.67; 128.92; 130.10; 131.67; 148.48; 153.57; 179.60; 202.64.

Example 7

(2S,7R)-trans-2-Isopropyl-7-[4-methoxy-3-(3-methoxypropoxy)benzyl]-8-methyl-non-4-enoic acid (I with R$^1$=3-methoxypropoxy and R$^2$=methoxy and X=OH)

To a solution of (2S,7S)-trans-2-isopropyl-7-[4-methoxy-3-(3-methoxypropoxy)-benzoyl]-8-methylnon-4-enoic acid (1.4 g; 3.2 mmol) in 1,2-dichloroethane were added triethylsilane (3.7 g; 32 mmol) and boron trifluoride diethyl etherate (2.7 g; 19.2 mmol), and the solution was stirred at 33° C. for 3 days. The reaction mixture was added to water and the aqueous layer was extracted 3× with tert-butyl methyl ether. The organic layer was dried over MgSO$_4$ and concentrated under reduced pressure. The remaining residue was purified by flash chromatography (silica gel; hexane/acetone 4:1) to obtain (2S,7R)-trans-2-isopropyl-7-[4-methoxy-3-(3-methoxypropoxy)benzyl]-8-methylnon-4-enoic acid (0.97 g, 2.3 mmol, 72% yield). The NMR data are identical to the data described in US2003/0149303 A1.

Example 8

(2S,7S)-trans-2-Isopropyl-7-[4-methoxy-3-(3-methoxypropoxy)benzoyl]-8-methyl-non-4-enoic acid (IV with R$^1$=3-methoxypropoxy and R$^2$=methoxy and X=OH)

To a cooled (−78° C.) solution of 4-bromo-1-methoxy-2-(3-methoxypropyloxy)-benzene (III with R$^1$=1-methoxy-3-propoxy and R$^2$=methoxy and Y=Br) (1.1 g; 3.9 mmol) in dry THF (6 ml) was added dropwise n-BuLi (2.8 ml; 1.6 M in hexane), and the reaction mixture was stirred at −78° C. for 45 min. This reaction mixture was added slowly to a cooled (−78° C.) suspension of (2S,7S)-trans-2,7-diisopropyloct-4-enedionyl chloride (1.0 g; 3.4 mmol) and CuI (65 mg, 0.34 mmol) in dry THF (4 ml). The reaction mixture was stirred at −78° C. for 45 min, warmed to RT and stirred for a further 2 h. After addition of water (20 ml), the reaction mixture was stirred for 1 h and then acidified with HCl. The aqueous layer was extracted 3× with tert-butyl methyl ether and the organic layer was dried over MgSO$_4$ and concentrated under reduced pressure. The crude residue was purified by flash chromatography (hexane, tert-butyl methyl ether 3:1+0.5% acetic acid) to obtain the title compound (IV) (0.296 g; 0.68 mmol; 20% yield) as a pale yellow oil. (2S,7S)-trans-2,7-Diisopropyloct-4-enedionic acid (0.21 g; 0.82 mmol; 24% yield) was likewise isolated and reused.

Example 9

(2S,7R)-trans-2-Isopropyl-7-[4-methoxy-3-(3-methoxypropoxy)benzyl]-8-methyl-non-4-enoic acid (I with $R^1$=3-methoxypropoxy and $R^2$=methoxy and X=OH)

To a solution of (2S,7S)-trans-2-isopropyl-7-[4-methoxy-3-(3-methoxypropyloxy)-benzoyl]-8-methylnon-4-enoic acid (90 mg; 0.21 mmol) in trifluoroacetic acid (1 ml) was added triethylsilane (250 µl; 1.5 mmol). After stirring the solution at RT for 1 day, a second portion of triethylsilane (250 µl; 1.5 mmol) was added, and the solution was stirred at RT for a further 2 days and then added to water. The aqueous layer was extracted 3× with tert-butyl methyl ether and the organic layer was dried over $MgSO_4$ and concentrated under reduced pressure. The crude residue was purified by flash chromatography (silica gel; hexane/acetone 4:1) to obtain (2S,7R)-trans-2-isopropyl-7-[4-methoxy-3-(3-methoxypropoxy)benzyl]-8-methylnon-4-enoic acid (53 mg, 0.126 mmol, 61% yield).

Example 10 rac-(2S,7S)-trans-2,7-Diisopropyloct-4-ene-1,8-dionic acid dimethyl ester (IIe with W=OMe):

To a mixture of rac-(2S,7S)-trans-2,7-diisopropyloct-4-ene-1,8-dionic acid (5.13 g; 20 mmol) in dichloromethane (55 ml) was added oxalyl chloride (7.62 g; 60 mmol), and the mixture was stirred at room temperature for 20 h. Methanol (3.2 g; 100 mmol) was then added slowly and the mixture was stirred at RT for 3 h. The reaction mixture was concentrated under reduced pressure. Water (30 ml) was added to the residue and the mixture was extracted with tert-butyl methyl ether (TBME) (3*30 ml). The organic phase was washed with 5% aqueous NaOH solution (5 ml), dried over $MgSO_4$ and concentrated under reduced pressure. rac-(2S,7S)-trans-2,7-Diisopropyloct-4-ene-1,8-dionic acid dimethyl ester was obtained as a colorless oil (5.58 g, 98% of theory).

$^1$H NMR ($CDCl_3$, 400 MHz): δ=0.85-0.95 (m, 12H); 1.84 (m, 2H); 2.12-2.29 (m, 6H); 3.65 (s, 6H); 5.38 (m, 2H).

$^{13}$C NMR ($CDCl_3$, 100.6 MHz): δ=20.27, 20.43; 30.19; 32.78, 51.08; 52.79; 129.36; 175.46.

Example 11 rac-(2S,7S)-trans-2,7-Diisopropyloct-4-ene-1,8-dionic acid monomethyl ester (IIf with $R^{13}$=Me; W=OH)

To a solution of rac-(2S,7S)-trans-2,7-diisopropyloct-4-ene-1,8-dionic acid dimethyl ester (1.85 g; 6.5 mmol) in methanol (10 ml) was added sodium hydroxide (0.286 mg; 7.15 mmol) in water (1.5 ml), and the mixture was stirred at 60° C. for 4 h. Subsequently, the mixture was cooled to room temperature and stirred for a further 16 h. The reaction mixture was then diluted with water (40 ml) and subsequently extracted with TBME (3×15 ml). The organic phase was dried over $MgSO_4$ and concentrated under reduced pressure, and unreacted starting material rac-(2S,7S)-trans-2,7-diisopropyloct-4-ene-1,8-dionic acid dimethyl ester (0.72 mg; 2.5 mmol) was removed and can be reused. The aqueous phase was acidified with 4N hydrochloric acid and extracted with TBME (3×15 ml). The organic phase of this acidic extraction was dried over $MgSO_4$ and concentrated under reduced pressure. A colorless oil was obtained (1.10 g). Purification by means of column chromatography (silica gel, pentane/isopropyl acetate 4:1) afforded rac-(2S,7S)-trans-2,7-diisopropyloct-4-ene-1,8-dionic acid monomethyl ester (0.74 g; 2.74 mmol; 42% of theory; 70% based on the conversion). Additionally obtained was also rac-(2S,7S)-trans-2,7-diisopropyloct-4-ene-1,8-dionic acid (0.16 g; 0.62 mmol; 10%), which can be reused, for example, in the synthesis according to example 10.

$^1$H NMR ($CDCl_3$, 400 MHz): δ=0.88-0.97 (m, 12H); 1.85 (m, 2H); 2.12-2.31 (m, 6H); 3.66 (s, 3H); 5.43 (m, 2H).

$^{13}$C NMR ($CDCl_3$, 100.6 MHz): δ=20.11; 20.17; 20.26; 20.32; 29.93; 30.20; 32.33; 32.82; 51.16; 52.48; 52.54; 52.83; 129.13; 129.64; 175.63; 180.71.

Example 12

Acid chloride of rac-(2S,7S)-trans-2,7-diisopropyloct-4-ene-1,8-dionic acid monomethyl ester (IIf with $R^{13}$=Me; W=Cl)

To a solution of rac-(2S,7S)-trans-2,7-diisopropyloct-4-ene-1,8-dionic acid monomethyl ester (0.74 g; 2.74 mmol) in dichloromethane (10 ml) was added oxalyl chloride (522 mg; 4.11 mmol), and the mixture was stirred at RT for 16 h. The mixture was concentrated under reduced pressure and coevaporated twice with methylcyclohexane. This afforded the acid chloride of rac-(2S,7S)-trans-2,7-diisopropyloct-4-ene-1,8-dionic acid monomethyl ester (0.79 g; quant.) as a colorless oil, which can be used further without purification.

Example 13 trans-2-Isopropyl-7-[4-methoxy-3-(3-methoxypropoxy)benzoyl]-8-methylnon-4-enoic acid methyl ester (IV with $R^{13}$=Me according to scheme 2)

To a cooled (−78° C.) solution of 4-bromo-1-methoxy-2-(3-methoxypropyloxy)-benzene (8.25 g; 30 mmol) in dry tetrahydrofuran (THF) (25 ml) was added dropwise n-BuLi (20 ml; 1.6 M in hexane), and the reaction mixture was stirred at −78° C. for 30 min. A freshly prepared solution of $MgCl_2$ (90 ml; 0.505 M in THF) was then added slowly and the mixture was stirred at −78° C. for 30 min. The mixture was warmed to room temperature with stirring within 30 min and stirred for a further 30 min. This reaction mixture was then added slowly to a cooled (−78° C.) suspension of the acid chloride of trans-2,7-diisopropyloct-4-ene-1,8-dionic acid monomethyl ester (8.33 g; 28.8 mmol) and CuI (560 mg, 2.9 mmol) in dry tetrahydrofuran (40 ml). The reaction mixture was stirred at −78° C. for 40 min, warmed to RT and stirred for a further 16 h. After adding water (200 ml), the reaction mixture was stirred for 1 h and then acidified with HCl. The aqueous phase was extracted with tert-butyl methyl ether (5×100 ml), and the organic phase was washed with 5% aqueous sodium hydroxide solution (50 ml) and then with saturated sodium chloride solution (50 ml), dried over $MgSO_4$ and concentrated under reduced pressure. The crude residue (12 g) was purified by flash chromatography (pentane/acetone 8:1) to obtain trans-2-isopropyl-7-[4-methoxy-3-(3-methoxypropoxy)benzoyl]-8-methylnon-4-enoic acid (1.55 g; 3.5 mmol, 12%) as a pale yellow oil.

$^1$H NMR ($CDCl_3$, 400 MHz): δ=0.80-0.95 (m, 12H); 1.75 (m, 1H); 1.90-2.30 (m, 7H); 2.45 (m, 1H); 3.22 (m, 1H); 3.37 (s, 3H); 3.57 (dd, 2H); 3.64 (s, 3H); 3.93 (s, 3H); 4.19 (dd, J1=J2=7 Hz, 2H); 5.35 (m, 2H); 6.88 (d, J=9 Hz, 1H); 7.54 (m, 2H).

The invention claimed is:
1. A process for preparing compounds of the general formula (I)

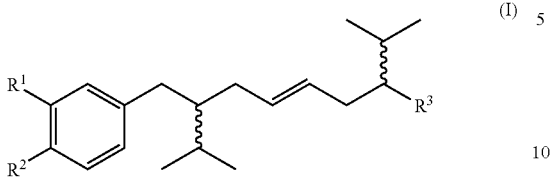

in which
R$^1$ and R$^2$ are each independently hydroxyl, alkoxy, aryloxy, arylalkyloxy or alkoxyalkoxy, the latter four groups each being unsubstituted or substituted;
R$^3$ is a heterocarbon group containing at least one heteroatom selected from O and N with at least one carbon-heteroatom multiple bond at the C-1 position, said group being bonded via the C-1 atom and being selected from COOR$^6$,
in which R$^6$ is hydrogen, alkyl, aryl, arylalkyl or trialkylsilyl, wherein the alkyl and the aryl may each be unsubstituted or substituted;
nitrile;
C(O)R$^7$,
in which R$^7$ is selected from
hydrogen, halogen, O$^-$, OM,
in which M is an alkali metal or an equivalent of an alkaline earth metal,
OCOR$^{12}$,
in which R$^{12}$ is unsubstituted or substituted branched lower alkyl having from 1 to 5 carbon atoms, or pivaloyl,
OCOCF$_3$, OSO$_2$CH$_3$ or OSO$_2$CF$_3$;
or R$^3$ comprises a protecting or activating group customary for carboxylic acids,
or is C(O)NR$^4$R$^5$,
in which R$^4$ and R$^5$ are independently hydrogen, alkyl, aryl, arylalkyl, or trialkylsilyl, wherein the alkyl and the aryl may each be unsubstituted or substituted,
or R$^4$ and R$^5$ together with the nitrogen form a five- to six-membered heterocyclic ring system which may optionally have from 1 to 3 additional heteroatoms;
or salts thereof,
wherein a compound of the general formula (II)

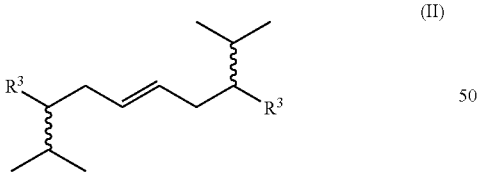

in which
R$^3$ is in each case independently as defined above under the formula (I);
is reacted in an addition reaction with a compound of the formula (III)

in which
Y is halogen, metal, metal halide, metal alkoxide or metal carboxylate,
R$^1$ and R$^2$ are each as defined above under the formula (I),
to obtain a compound of the formula (IV)

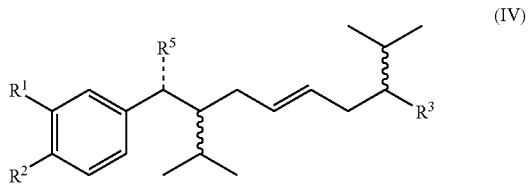

in which
R$^1$, R$^2$ and R$^3$ are each as defined above under the formula (I);
the dotted line represents a single or double bond;
R$^5$ is O or NR$^8$ in which R$^8$ is hydrogen or unsubstituted or substituted alkyl if the dotted line represents a double bond, or
R$^5$ is OH or NR$^8$R$^9$ in which R$^8$ and R$^9$ are each independently hydrogen, alkyl or aryl or alkylaryl, each being unsubstituted or substituted if the dotted line represents a single bond;
and the compound of the formula (IV) is subjected to at least one reduction reaction to obtain the desired product of the formula (I),
wherein substituted means substituted by one or more of the following groups selected from halogen, hydroxyl, cyano, C$_1$-C$_6$-alkoxy, nitro, amino, C$_1$-C$_6$-alkylamino, di-C$_1$-C$_6$-alkylamino, carboxyl, C$_1$-C$_6$-alkoxycarbonyl, aminocarbonyl, halomethyl, dihalomethyl, trihalomethyl, haloethyl, dihaloethyl, trihaloethyl, tetrahaloethyl, and pentahaloelhyl.

2. The process of claim 1, in which the compound of the formula (II) is used as a mixture of the isomers.

3. The process of claim 1, comprising an additional isomer separation step before or after one of the addition or reduction steps and optionally additionally an isomerization or racemization of the undesired isomers.

4. The process as claimed in claim 1, in which the radicals in the formula (I) are each defined as follows:
R$^1$: hydroxyl or unsubstituted or substituted branched or unbranched lower alkoxy having from 1 to 5 carbon atoms, unsubstituted or substituted aryloxy or unsubstituted or substituted branched or unbranched alkoxyalkoxy having in each case from 1 to 5 carbon atoms in the alkoxy group,
R$^2$: hydroxyl or unsubstituted or substituted branched or unbranched lower alkoxy having from 1 to 5 carbon atoms, unsubstituted or substituted aryloxy or unsubstituted or substituted branched or unbranched alkoxyalkoxy having in each case from 1 to 5 carbon atoms in the alkoxy group,
and
R$^3$: COOR$^6$ in which R$^6$ is hydrogen, branched or unbranched lower alkyl having from 1 to 5 carbon atoms, aryl, benzyl or trialkylsilyl, wherein the alkyl and the aryl may each be unsubstituted or substituted, nitrile, C(O)R$^7$ in which R$^7$ is hydrogen, halogen, O$^-$, OM in which M is an alkali metal or an equivalent of an alkaline earth metal, or C(O)NR$^4$R$^5$ in which R$^4$ and R$^5$ are independently unsubstituted or substituted branched or unbranched lower alkyl having from 1 to 5 carbon atoms, or benzyl.

5. The process of claim 3, in which the compound of the formula (I) corresponds to the formula (VI)

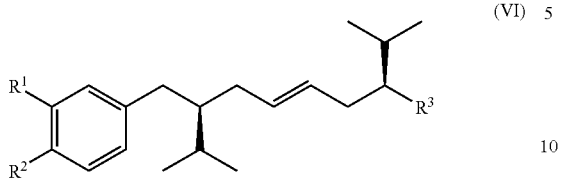

in which $R^1$, $R^2$ and $R^3$ are each as defined above under formula (I).

6. The process of claim 5, in which the compound of the formula (I) corresponds to the formula (VII)

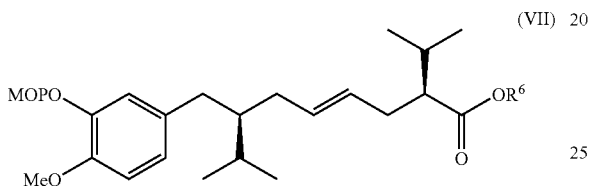

in which

MOPO is methoxypropoxy and $R^6$ is as defined above under formula (I).

7. The process as claimed in claim 1, in which $R^3$ is independently

COOR$^6$, in which $R^6$ is hydrogen, alkyl, aryl, arylalkyl or trialkylsilyl, wherein the alkyl and the aryl may each be unsubstituted or substituted;

nitrile;

C(O)R$^7$, in which $R^7$ is halogen, O$^-$, OM, in which M is an alkali metal or an equivalent of an alkaline earth metal.

8. The process as claimed in claim 1, in which the addition reaction is carried out with a compound of the formula (III) in which Y is Li, Na, CuCl, CuBr, CuI, MgCl or MgBr.

9. The process as claimed in claim 1, in which the reduction is carried out in one or two steps with metal hydride or trialkylsilane in the presence of acids or with Lewis acids.

10. The process of claim 6, in which the compound of the formula (VII) is converted in an additional amidation to the compound of the formula (VIII)

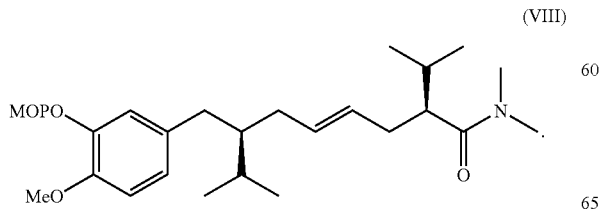

11. Compounds of the formula (IV)

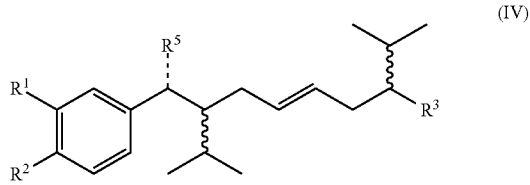

in which $R^1$ and $R^2$ are each independently hydroxyl, alkoxy, aryloxy, arylalkyloxy or alkoxyalkoxy, the latter four groups each being unsubstituted or substituted;

$R^3$ is a heterocarbon group containing at least one heteroatom selected from O and N with at least one carbon-heteroatom multiple bond at the C-1 position, said group being bonded via the C-1 atom and being selected from COOR$^6$, in which $R^6$ is hydrogen, alkyl, aryl, arylalkyl or trialkylsilyl, wherein the alkyl and the aryl may each be unsubstituted or substituted;

nitrile;

C(O)R$^7$, in which $R^7$ is selected from hydrogen, halogen, O$^-$, OM, in which M is an alkali metal or an equivalent of an alkaline earth metal,

OCOR$^{12}$, in which $R^{12}$ is unsubstituted or substituted branched lower alkyl having from 1 to 5 carbon atoms, or pivaloyl, OCOCF$_3$, OSO$_2$CH$_3$ or OSO$_2$CF$_3$;

or $R^3$ comprises a protecting or activating group customary for carboxylic acids, or is C(O)NR$^4$R$^5$, in which $R^4$ and $R^5$ are independently hydrogen, alkyl, aryl, arylalkyl, or trialkylsilyl, wherein the alkyl and the aryl may each be unsubstituted or substituted, or $R^4$ and $R^5$ together with the nitrogen form a five- to six-membered heterocyclic ring system which may optionally have from 1 to 3 additional heteroatoms;

or salts thereof;

the dotted line represents a single or double bond;

$R^5$ is O or NR$^8$ in which $R^8$ is hydrogen or unsubstituted or substituted alkyl if the dotted line represents a double bond, or $R^5$ is OH or NH$_2$ if the dotted line represents a single bond, or salts thereof, wherein substituted means substituted by one or more of the following groups selected from halogen, hydroxyl, cyano, C$_1$-C$_6$-alkoxy, nitro, amino, C$_1$-C$_6$-alkylamino, di-C$_1$-C$_6$-alkylamino, carboxyl, C$_1$-C$_6$-alkoxycarbonyl, aminocarbonyl, halomethyl, dihalomethyl, trihalomethyl, haloethyl, dihaloethyl, trihaloethyl, tetrahaloethyl, and penlahaloethyl.

12. The compounds of the formula (IV)

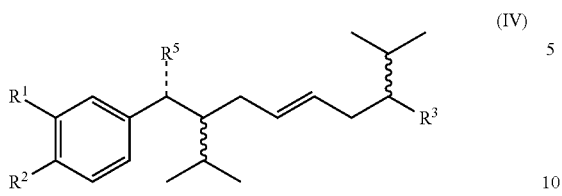

in which

R¹ and R² are each independently hydroxyl, alkoxy, aryloxy, arylalkyloxy or alkoxyalkoxy, the latter four groups each being unsubstituted or substituted;

R³ is a heterocarbon group containing at least one heteroatom selected from O and N with at least one carbon-heteroatom multiple bond at the C-1 position, said group being bonded via the C-1 atom and being selected from COOR⁶, in which R⁶ is hydrogen, alkyl, aryl, arylalkyl or trialkylsilyl, wherein the alkyl and the aryl may each be unsubstituted or substituted;

nitrile;

C(O)R⁷, in which R⁷ is selected from hydrogen, halogen, O⁻, OM, in which M is an alkali metal or an equivalent of an alkaline earth metal,

OCOR¹², in which R¹² is unsubstituted or substituted branched lower alkyl having from 1 to 5 carbon atoms, or pivaloyl, OCOCF₃, OSO₂CH₃ or OSO₂CF₃;

or R³ comprises a protecting or activating group customary for carboxylic acids, or is C(O)NR⁴R⁵, in which R⁴ and R⁵ are independently hydrogen, alkyl, aryl, arylalkyl, or trialkylsilyl, wherein the alkyl and the aryl may each be unsubstituted or substituted, or R⁴ and R⁵ together with the nitrogen form a five- to six-membered heterocyclic ring system which may optionally have from 1 to 3 additional heteroatoms;

or salts thereof;

the dotted line represents a single or double bond;

R⁵ is O or NR⁸ in which R⁸ is hydrogen or unsubstituted or substituted alkyl if the dotted line represents a double bond, or R⁵ is OH or NH, if the dotted line represents a single bond, or salts thereof, as the (S,S)-enantiomers, wherein substituted means substituted by one or more of the following groups selected from halogen, hydroxyl, cyano, C₁-C₆-alkoxy, nitro, amino, C₁-C₆-alkylamino, di-C₁-C₆-alkylamino, carboxyl, C₁-C₆-alkoxycarbonyl, aminocarbonyl, halomethyl, dihalomethyl, trihalomethyl, haloethyl, dihaloethyl, trihaloethyl, tetrahaloethyl, penlahaloethyl.

13. The process as claimed in claim 1 for preparing compounds of the general formula (I)

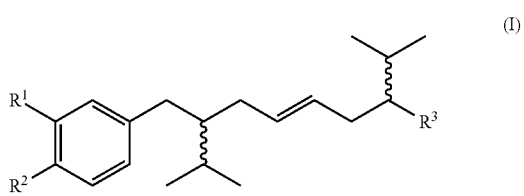

in which

R¹ and R² are each independently hydroxyl, alkoxy, aryloxy, arylalkyloxy or alkoxyalkoxy, the latter four groups each being unsubstituted or substituted;

R³ is COOR⁶ in which R⁶ is hydrogen, alkyl, aryl, arylalkyl or trialkylsilyl, wherein the alkyl and the aryl may be unsubstituted or substituted;

nitrile;

C(O)R⁷, in which R⁷ is selected from halogen O⁻, OM, in which M is an alkali metal or an equivalent of an alkaline earth metal,

OCOR¹² in which R¹² is unsubstituted or substituted branched lower alkyl having from 1 to 5 carbon atoms, or pivaloyl, OSO₂CH₃ or OSO₂CF₃;

or salts thereof, wherein a compound of the general formula (II)

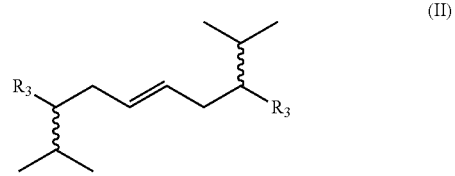

in which

R³ is in each case independently as defined above under the formula (I);

is reacted in an addition reaction with a compound of the formula (III)

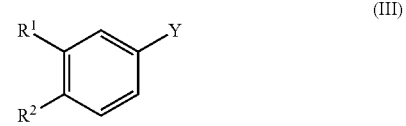

in which

Y is halogen, metal, metal halide, metal alkoxide or metal carboxylate, preferably Li, Na, Mg, Zn, Cu and B, R¹ and R² are each as defined above under the formula (I), to obtain a compound of the formula (IV)

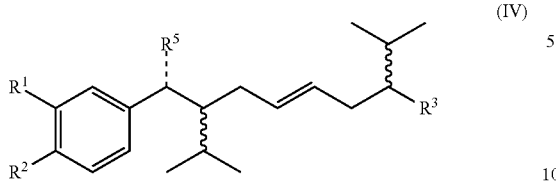

(IV)

in which
R¹ and R² are each independently hydroxyl, alkoxy, aryloxy, arylalkyloxy or alkoxyalkoxy, the latter four groups each being unsubstituted or substituted;
R³ is a heterocarbon group containing at least one heteroatom selected from O and N with at least one carbon-heteroatom multiple bond at the C-1 position, said group being bonded via the C-1 atom and being selected from COOR⁶,
  in which R⁶ is hydrogen, alkyl, aryl, arylalkyl or trialkylsilyl, wherein the alkyl and the aryl may each be unsubstituted or substituted;
nitrile;
C(O)R⁷,
  in which R⁷ is selected from
  hydrogen, halogen, O⁻, OM,
    in which M is an alkali metal or an equivalent of an alkaline earth metal,
  OCOR¹²,
    in which R¹² is unsubstituted or substituted branched lower alkyl having from 1 to 5 carbon atoms, or pivaloyl,
  OCOCF₃, OSO₂CH₃ or OSO₂CF₃;
or R³ comprises a protecting or activating group customary for carboxylic acids, or is C(O)NR⁴R⁵,
  in which R⁴ and R⁵ are independently hydrogen, alkyl, aryl, arylalkyl, or trialkylsilyl, wherein the alkyl and the aryl may each be unsubstituted or substituted,
  or R⁴ and R⁵ together with the nitrogen form a five- to six-membered heterocyclic ring system which may optionally have from 1 to 3 additional heteroatoms;
or salts thereof;
the dotted line represents a double bond;
R⁵ is O;
and the compound of the formula (IV) is subjected to at least one reduction reaction to obtain the desired product of the formula (I).

14. The process as claimed in claim 1, wherein the protecting or activating group customary for carboxylic acids is selected form C(O)N-alkyl-O-alkyl.

15. The process as claimed in claim 4, in which the radicals R¹ and R² in the formula (I) are each defined as follows:
R¹: hydroxyl or unsubstituted or substituted methoxy, ethoxy, n- and i-propoxy, n-, i- and t-butoxy or pentoxy, unsubstituted or substituted phenyloxy, naphthyloxy or derivatives thereof, or benzyloxy or unsubstituted or substituted 1-methoxymethoxy, 1-methoxy-2-ethoxy, 1-methoxy-3-propoxy, 1-methoxy-4-butoxy,
and
R²: hydroxyl or unsubstituted or substituted methoxy, ethoxy, n- and i-propoxy, n-, i- and t-butoxy or pentoxy, unsubstituted or substituted phenyloxy, naphthyloxy or derivatives thereof, or benzyloxy or unsubstituted or substituted 1-methoxymethoxy, 1-methoxy-2-ethoxy, 1-methoxy-3-propoxy, 1-methoxy-4-butoxy.

16. The process as claimed in claim 1, in which R⁶ in Group COOR⁶ is hydrogen.

* * * * *